United States Patent [19]
Bull et al.

[11] Patent Number: 5,756,480
[45] Date of Patent: May 26, 1998

[54] TREATMENT OF HYPERANDROGENIC CONDITIONS

[75] Inventors: Herb G. Bull, Westfield; Georgianna Harris, Tinton Falls; Robert W. Myers, Cresskill, all of N.J.

[73] Assignee: Merck & Co., Inc., Rahway, N.J.

[21] Appl. No.: 738,546

[22] Filed: Oct. 24, 1996

[51] Int. Cl.$^6$ .................. C07H 19/04; C07H 19/048; A61K 31/705
[52] U.S. Cl. .................. 514/47; 536/26.2; 536/26.26; 546/281.1; 546/283.1
[58] Field of Search .................. 536/26.2, 26.26; 514/47; 546/281.1, 283.1

[56] References Cited

U.S. PATENT DOCUMENTS

| | | | |
|---|---|---|---|
| 3,644,421 | 2/1972 | Cross | 549/275 |
| 4,760,071 | 7/1988 | Rasmusson et al. | 514/284 |
| 5,075,450 | 12/1991 | Rasmusson et al. | 546/285 |
| 5,084,574 | 1/1992 | Bhattacharya et al. | 546/77 |
| 5,091,380 | 2/1992 | Rasmusson et al. | 514/169 |

FOREIGN PATENT DOCUMENTS

WO 96/20713  7/1996  WIPO.

OTHER PUBLICATIONS

Wall Street Journal, May 7, 1996, p. B4, "Study finds Abbott's prostate drug is much more effective than Merck's".

The Daily, Tuesday, May 7, 1996, "New data on Proscar, Abbott's Hytrin show conflicting results".

Tian et al., Biochemistry, vol. 33 (1994), pp. 2291–2296, "17beta–(N–tert–butylcarbamoyl)–4–aza–5alpha–androstan–1–en–3–one is an active site–directed slow time–dependent inhibitor of human steriod 5alpha–reductase 1".

Everse et al., Bioorganic Chemistry, vol. 1 (1971), pp. 207–233, "Addition products of diphosphopyridine nucleotides with substrates of pyridine nucleotide–linked dehydrogenases".

Bull et al., J. Am. Chem. Soc., vol. 118 (1996), pp. 2359–2365, "Mechanism–based inhibition of human steroid 5alpha–reductase by finasteride".

Faller et al., Biochemistry, vol. 32 (1993), pp. 5705–5710, "Finasteride: A slow–binding 5alpha–reductase inhibitor".

Baginsky et al., FASEB J., vol. 8 (1994), p. 638, "Mechanism of inhibition of human prostatic 5alpha–reductase by 4–azasteroids".

Barton et al., J. of the Chem. Soc., Perkin Trans. 1, No. 8 (1982), pp. 1919–1922, "Dehydrogenation of lactones using benzeneseleninic anhydride."

Barton et al., Tetrahedron Letters, No. 35 (1979), pp. 3331–3334, "Preparation of aldehydes and ketones by oxidation of benzylic hydrocarbons with benzeneseleninic anhydride."

Primary Examiner—Alan L. Rothman
Attorney, Agent, or Firm—Catherine D. Fitch; William H. Nicholson

[57] ABSTRACT

The invention concerns the treatment of hyperandrogenic conditions in humans by the formation of a novel mechanism-based irreversible inhibitor of human 5α-reductase enzymes from 3-oxo-4-oxa end 4-thiasteroids having a 1,2-double bond and the pyridine-nucleotide cofactor of the 5α-reductase enzyme, NADPH. The invention further relates to the isolated inhibitor-cofactor complex.

8 Claims, No Drawings

TREATMENT OF HYPERANDROGENIC CONDITIONS

CROSS-REFERENCE

This application claims the benefit of Provisional Application No. 60/005,869 filed Oct. 26, 1965.

SUMMARY OF THE INVENTION

The invention concerns the treatment of hyperandrogenic conditions in humans by the formation of a novel mechanism-based irreversible inhibitor of human 5α-reductase enzymes from 3-oxo-4-oxa and 4-thiasteroids having a 1,2-double bond and the pyridine-nucleotide cofactor of the 5α-reductase enzyme, NADPH. The invention further relates to the isolated inhibitor-cofactor complex.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endocrinol. 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of testosterone-5α-reductase. Inhibitors of testosterone-5α-reductase will serve to prevent or lessen symptoms of hyperandrogenic stimulation in these organs.

The enzyme 5α-reductase catalyzes the reduction of testosterone to the more potent androgen, dihydrotestosterone, as shown below:

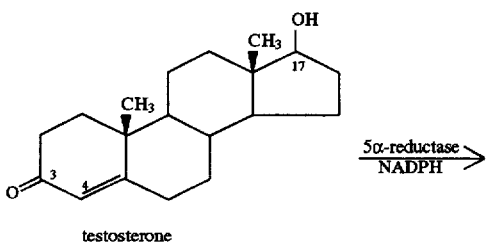

testosterone

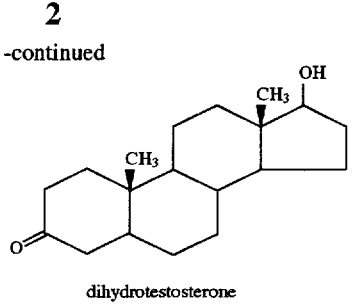

dihydrotestosterone

Finasteride, (17β-(N-tert-butylcarbamoyl)-3-oxo-4-aza-5α-androst-1-ene-3-one) as shown below, is a potent inhibitor of the human prostate enzyme.

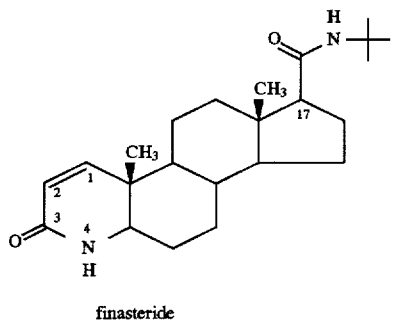

finasteride

Under the trade name PROSCAR®, finasteride is known to be useful in the treatment of hyperandrogenic conditions; see eg. U.S. Pat. No. 4,760,071. Finasteride is currently prescribed for the treatment of benign prostatic hyperplasia (BPH), a condition afflicting to some degree the majority of men over age 55. Finasteride's utility in the treatment of androgenic alopecia and prostatic carcinoma is also disclosed in the following documents: EP 0 285,382, published 5 Oct. 1988; EP 0 285,383, published 5 Oct. 1988; Canadian Patent no. 1,302,277; and Canadian Patent no. 1,302,276.

There are two isozymes of 5α-reductase in humans. One isozyme (type 1) predominates in sebaceous glands of most regions of skin tissue and is relatively insensitive to finasteride; the other (type 2) predominates in the prostate and is potently inhibited by finasteride.

In clinical trials, the efficacy of finasteride far exceeded expectations based on its perceived potency against the human prostate enzyme, for which finasteride was first thought to be a simple, rapidly-reversible inhibitor with $K_i$=26 nM. For instance, circulating concentrations of finasteride comparable to this Ki actually reduced levels of dihydrotestosterone to values approaching those found in individuals genetically deficient in the prostate isozyme, and as long as two weeks were required for dihydrotestosterone to return to basal levels after withdrawal of finasteride (Stoner, J. Steroid. Biochem. Molec. Biol. 37: 375–378 (1990) and Gormley et al., J. Clin. Endocrinol. Metabol. 70: 1136–1141 (1990)). A closer evaluation of the interaction of finasteride with the human prostate (type 2) isozyme led to appreciation that finasteride and certain analogs thereof are slow-binding inhibitors, such that their potency had been mistakenly underrated in standard fixed-time assays (Harris et al., Proc. Natl. Acad. Sci. U.S.A., 89: 10787–10791 (1992)). Independently, Faller et al., also recognized the inconsistency. Faller et al., have recently described in detail the slow-binding behavior of finasteride, reaching the conclusion that finasteride binds to the human prostate isozyme with a rate constant of $2.7 \times 10^5 M^{-1} s^{-1}$ to form an essentially irreversible enzyme-inhibitor complex with a $K_i$<<1 nM (Faller et al., Biochemistry 32: 5705–5710 (1993)).

Although finasteride is not a significant inhibitor of human skin (type 1) isozyme at doses employed in the treatment of BPH, finasteride does slowly form a comparable high affinity complex with this isozyme. As determined by Tian, et al., Biochemistry 33: 2291–2296 (1994), the second-order rate constant for formation of this complex is $4.0 \times 10^3 M^{-1} s^{-1}$, which is about 1% of the rate constant against the prostate isozyme. Based on the apparent irreversible inhibition and on structure-activity considerations, Tian et al., proposed that finasteride binds to the enzyme covalently as a Michael acceptor. U.S. Ser. No. (08/368, 513), filed Jan. 4, 1995, describes that finasteride and other 3-oxo-4-aza steroids having a 1,2 double bond are mechanism-based irreversible inhibitors of 5α-reductase.

The present invention demonstrates, in contrast to the expectation in the art, that 3-oxo-4-oxa and 4-thiasteroids having a 1,2 double bond are novel mechanism-based irreversible inhibitors of 5α-reductase. These 3-oxo-4-oxa and 4-thiasteroids having a 1,2-double bond are recognized as a substrate by the human 5α-reductase type 1 and type 2 enzymes, and in the course of the enzymatic reduction, the 3-oxo-4-oxa and 4-thiasteroid having a 1,2-double bond forms a covalent adduct with the pyridine-nucleotide cofactor (NADPH). The covalent inhibitor-cofactor complex formed between the 3-oxo-4-oxasteroid anion and the oxidized nicotinamide cofactor is bound by the enzyme as a potent collected-product inhibitor.

Kaplan et al. averse et al., Bioorganic Chem. 1: 207–233 (1971)) in their work with pyridine nucleotide-linked dehydrogenases identified analogous high-affinity, abortive ternary complexes formed spontaneously (in the reverse direction) by several pyridine nucleotide-linked dehydrogenases, notably lactate dehydrogenase. Lactate dehydrogenase mistakenly adds pyruvate to $NAD^+$ to form the inhibitor shown below:

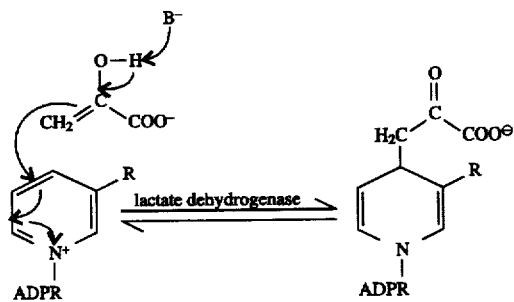

wherein B⁻ represents a basic group on the enzyme active site and ADPR represents adenosine-diphospho-ribose.

DETAILED DESCRIPTION OF THE INVENTION

Novel mechanism-based irreversible inhibitors of human 5α-reductase enzymes are formed from 3-oxo-4-oxa and 4-thiasteroids having a 1,2-double bond and the pyridine-nucleotide cofactor of the 5α-reductase enzyme NADPH. The structure of the covalent NADP-inhibitor complex, is represented below as structural formula (I):

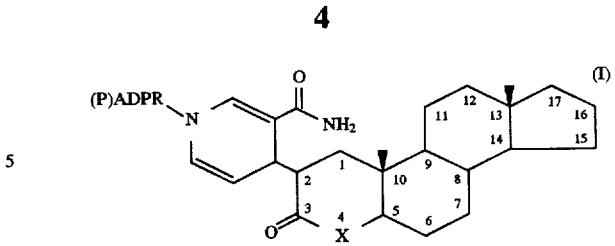

wherein X is oxygen or sulfur and (P)ADPR signifies 2-phosphoadenosine-diphospho-ribose.

The covalent adduct of structural formula (I) may optionally be modified as known to those in the art so long as the 3-oxo position and the oxygen or sulfur at the 4-position are conserved. Particularly preferred are compounds substituted at any of the following positions of the oxasteroid ring: 7,15,16 and 17, depending on the structure of the 3-oxo-4-oxa and 4-thiasteroid having a 1,2-double bond administered to the human being.

The mechanism for inhibition of the 5α-reductase enzyme is proposed in Scheme 1. There is a close parallel between reduction of the natural substrate, testosterone, and reduction of 3-oxo-4-oxa and 4-thiasteroid inhibitors having a 1,2-double bond, since both proceed through nearly identical high-energy transition states. In the case of testosterone, transfer of hydride ion to C-5 gives the 3,4-enolate, and the reduction is completed by transfer of a proton to C-4 to allow tautomerization to dihydrotestosterone. In the case of 3-oxo-4-oxa and 4-thiasteroid inhibitors having 1,2-double bond, transfer of hydride ion to C-1 gives the 2,3-enolate instead. It is certain that this hydride transfer is essentially complete in the high-affinity complex, since no untransformed 3-oxo-4-oxa and 4-thiasteroid inhibitor having a 1,2-double bond is recovered upon denaturation of the enzyme-inhibitor complex. At this point, the enzyme becomes trapped, being unprepared to transfer a proton to C-2 to complete the reduction. Unable to find a proton, the enolate/carbanion attacks the positively charged pyridinium ion of $NADP^+$ to produce the covalent adduct, which the enzyme binds tenaciously.

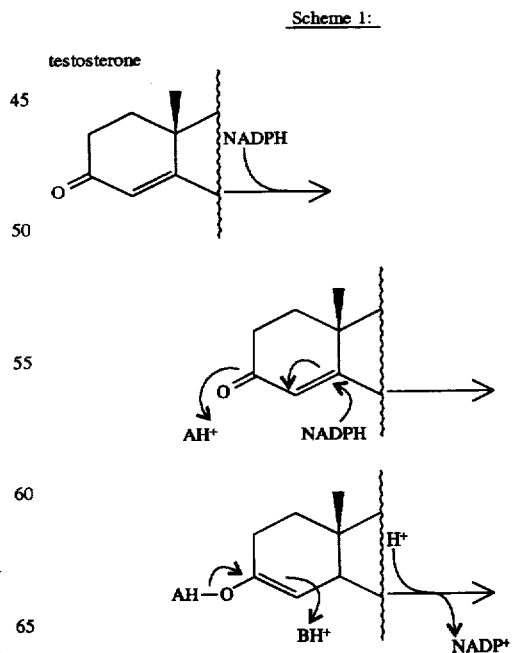

Scheme 1:

-continued
Scheme 1:

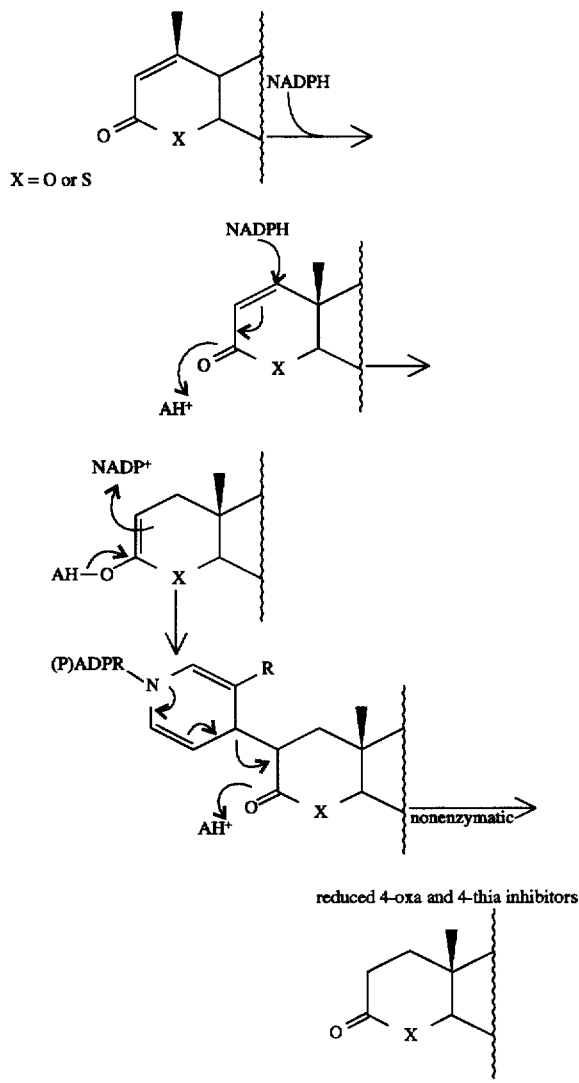

3-oxo-4-oxa and 4-thia inhibitors with 1,2-double bond reduced 4-oxa and 4-thia inhibitors In the scheme above, AH and BH represent proton donors in the enzyme active site and (P)ADPR represents 2-phospho-adenosine-diphospho-ribose.

3-oxo-4-oxa and 4-thiasteroids having a 1,2-double bond (also called $\Delta^1$-3-oxo-4-oxa and 4-thiasteroids and $\Delta^1$-3-oxo-4-thiasteroids) are selectively activated by the enzyme 5α-reductase to produce the novel covalent adduct with the cofactor NADPH of structural formula (I):

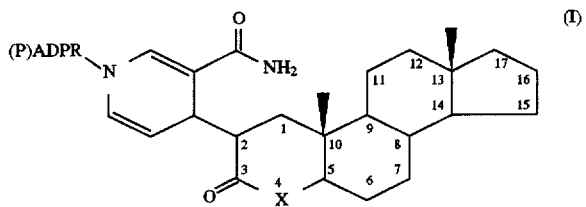

wherein X is oxygen or sulfur. Illustrating the 3-oxo-4-oxa and 4-thiasteroids having a 1,2-double bond useful in the present invention are the compounds of structural formula II, below:

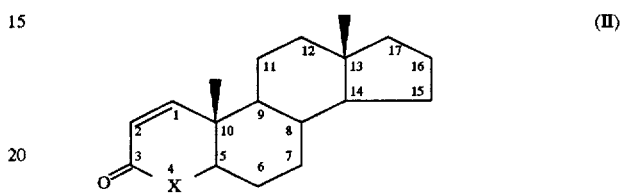

wherein X is oxygen or sulfur.

More particularly defining the 3-oxo-4-oxa and 4-thiasteroids having a 1,2-double bond useful in the present invention are the compounds of structural formula III, below:

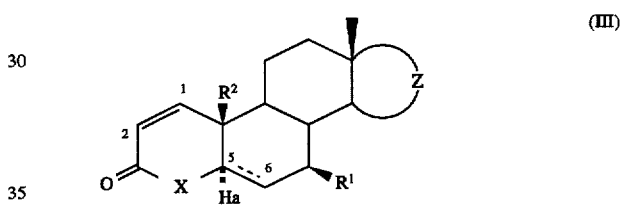

or a pharmaceutically acceptable salt, ester or stereoisomer thereof, wherein:

the C5–C6 bond designated with a dotted line independently represents a single or double bond, provided that when the C5–C6 is a double bond, $H_a$ is absent and when the C5–C6 bond is a single bond $H_a$ is present and represents hydrogen;

X is selected from oxygen and sulfur;
$R^1$ is selected from hydrogen and $C_{1-5}$ alkyl;
$R^2$ is selected from $CH_3$, $CH_2OR^3$, and H;
$R^3$ is selected from: $C_{1-5}$ alkyl;
Z is

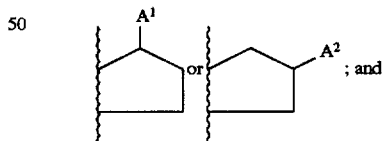

$A^1$ is selected from:
(1) —H,
(2) keto,
(6) carboxy,
(7) protected amino,
(8) amino,
(9) $C_{1-10}$alkyl,
(10) substituted or unsubstituted $C_{2-10}$alkenyl,
(11) aryl-substituted $C_{1-10}$ alkyl,
(12) aryl or heteroaryl,

(13) substituted aryl or heteroaryl,
(14) aryl or heteroaryl carbamoyl-substituted $C_{1-10}$alkyl,
(15) $C_{1-10}$alkylcarbonyl,
(16) aryl or heteroaryl carbonyl,
(17) ether-substituted $C_{1-10}$alkyl,
(18) thioether-substituted $C_{1-10}$alkyl,
(19) keto-substituted $C_{1-10}$alkyl,
(20) heteroaryl-substituted $C_{1-10}$ alkyl,
(21) carboxylic ester,
(22) carboxamide, including substituted and unsubstituted anilide derivatives,
(23) urea,
(24) $C_{1-10}$ alkylureido $C_{0-5}$ alkyl,
(25) substituted or unsubstituted heteroaryl or arylureido$C_{0-5}$ alkyl,
(26) $C_{1-10}$alkanoyloxy$C_{1-2}$alkyl,
(27) $C_{1-10}$ alkylcarbonylamino,
(28) alkanoylamidoalkyl
(29) ether,
(30) thio ether, and
(31) substituted and unsubstituted aryl or heteroaryl ether;
$A^2$ is selected from:
(1) —H,
(2) keto,
(3) protected hydroxy,
(4) acetate,
(5) hydroxy,
(6) carboxy,
(7) protected amino,
(8) amino,
(9) $C_{1-10}$alkyl,
(10) substituted or unsubstituted $C_{2-10}$alkenyl,
(11) aryl-substituted $C_{1-10}$alkyl,
(12) aryl or heteroaryl,
(13) substituted aryl or heteroaryl,
(14) aryl or heteroaryl carbamoyl-substituted $C_{1-10}$alkyl,
(15) $C_{1-10}$alkylcarbonyl,
(16) aryl or heteroaryl carbonyl,
(17) ether-substituted $C_{1-10}$alkyl,
(18) thioether-substituted $C_{1-10}$alkyl,
(19) keto-substituted $C_{1-10}$alkyl,
(20) heteroaryl-substituted $C_{1-10}$ alkyl,
(21) carboxylic ester,
(22) carboxamide, including substituted and unsubstituted anilide derivatives,
(23) urea,
(24) $C_{1-10}$alkylureido $C_{0-5}$alkyl,
(25) substituted or unsubstituted arylureido$C_{0-5}$ alkyl,
(26) $C_{1-10}$alkanoyloxy$C_{1-2}$alkyl,
(27) $C_{1-10}$alkylcarbonylamino,
(28) alkanoylamidoalkyl,
(29) ether,
(30) thio ether, and
(31) substituted and unsubstituted aryl- or heteroaryl-ether;

Heteroaryl is selected from piperidinyl, piperizinyl, pyrrolidinyl, pyrrolyl, furanyl, thienyl, pyridyl, pyrimidinyl, indolyl and benzofuranyl.

Preferred are compounds wherein:
(a) protected hydroxy is selected from: dimethyl-t-butyl silyloxy, trimethylsilyloxy, tri-ethylsilyloxy, tri-isopropylsilyloxy, and triphenylsilyloxy;
(b) protected amino is acetylamino, benzoylamino, and pivaloylamino;
(c) $C_{1-10}$alkyl is selected from methyl, ethyl, propyl, butyl, pentyl, 1,5-dimethylhexyl, 6-methylhept-2-yl, 5-methylhexyl, and 1-methyl-4-isopropylhexyl;
(d) substituted or unsubstituted $C_{2-10}$alkenyl is selected from: phenylmethylene, chlorophenylmethylene, ethoxycarbonylphenylmethylene, carboxyphenylmethylene, (((1,1-dimethylethyl)amino) carbonyl)phenylmethylene, trimethoxyphenyl methylene, methoxyphenylmethylene, methylsulfonylphenylmethylene, biphenylmethylene, nitrophenylmethylene, aminophenylmethylene, acetylaminophenylmethylene, pivaloylaminophenylmethylene, phenoxyphenylmethylene, 2-imidazolyl methylene, 2-thiazolylmethylene,
(e) aryl substituted $C_{1-10}$alkyl is selected from omega-phenylpropyl and 1-(chlorophenoxy)ethyl;
(f) aryl is selected from phenyl, and naphthyl;
(g) substituted aryl or heteroaryl is selected from phenyl, pyridyl and pyrimidinyl substituted with one to three substituents independently selected from:
(1) —H,
(2) —OH,
(3) —$CH_3$,
(4) —$OCH_3$,
(5) —$S(O)_n$—$CH_3$, wherein n is selected from 0, 1, and 2,
(6) —$CF_3$,
(7) halo,
(8) —CHO,
(9) CN,
(10) phenyloxy,
(11) ethyl,
(12) t-butyl,
(13) $OCH_2CH_3$,
(14) $OC(CH_3)_3$, and
(15) —$NHR_7$, wherein $R^7$ is selected from: —H, —$C_{1-8}$ alkyl, —$C_{1-6}$ alkylcarbonyl, —$C_{1-6}$ alkylsulfonyl, and —$C_{1-6}$alkoxycarbonyl,
(h) aryl or heteroaryl carbamoyl substituted $C_{1-10}$alkyl is selected from 2-(4-pyridyl-carbamoyl)ethyl and 2-phenyl-ethyl;
(i) $C_{1-10}$alkylcarbonyl is selected from isobutylcarbonyl and isopropylcarbonyl;
(j) aryl or heteroaryl carbonyl is selected from phenylcarbonyl and pyridyl carbonyl;
(k) ether-substituted $C_{1-10}$alkyl is selected from 1-methoxy-ethyl and 1-ethoxy-ethyl;
(l) thioether-substituted $C_{1-10}$alkyl is selected from 1-methylthio-ethyl, and 1-ethylthio-ethyl;
(m) keto-substituted $C_{1-10}$alkyl is 1-keto-ethyl, ketomethyl, 1-ketopropyl, and ketobutyl;
(n) heteroaryl-substituted $C_{1-10}$alkyl is omega-(4-pyridyl)-butyl;
(o) carboxylic esters are $C_{1-10}$alkylcarboxylic esters selected from carbomethoxy and carboethoxy;
(p) carboxamides are selected from N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy) phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-diphenylmethyl) carboxamide, N-(diphenylmethyl)-carboxamide, N-t-butyl carboxamide, N-isopropyl carboxamide, 1-adamantyl carboxamide, 2-adamantyl carboxamide and N-(substituted phenyl) carboxamides wherein the phenyl may be substituted with 1 to 2 substitutents selected from ethyl, methyl, trifluoromethyl or halo (F, Cl, Br, I);

(q) $C_{1-10}$alkanoyloxy$C_{1-2}$alkyl is selected from acetyloxymethyl, trimethylacetyloxymethyl, and (2-ethylhexanoyloxy)methyl;

(r) urea is t-butylcarbonylamino urea;

(s) $C_{1-10}$ alkylureido $C_{0-5}$ alkyl is selected from: N-t-butylureidomethyl, N-n-propylureidomethyl, N-n-octylureidomethyl, N-isopropylureido, allylureido, (t) substituted or unsubstituted arylureido$C_{0-5}$alkyl is selected from: N-(ethylphenyl) ureidomethyl, N-(chlorophenyl) ureidomethyl, N-phenylureidomethyl, N-(dichlorophenyl) ureidomethyl, N-naphth-2-yl ureidomethyl, N-thiazol-2-ylureidomethyl, N-thien-2-ylmethylureidomethyl, N-(fluorophenyl)ureido, N-(methoxyphenyl)ureido, and 2-(ethoxyphenyl) ureidomethyl;

(u) $C_{1-10}$alkylcarbonylamino is t-butylcarbonylamino;

(v) alkanoylamidoalkyl is selected from: trimethylacetamidomethyl, carbomethoxyoctanoylamidomethyl, (isobutylphenyl) propionamidomethyl, 8-carboxyoctanoylamidomethyl, bromohexanoylamido methyl, hydroxydodecanoyl amidomethyl, 4-nitrophenylprionamidomethyl, isopropylthioacetamidomethyl, benzyloxyacetamidomethyl, carbomethoxyacetamidomethyl, triphenylproprionamidomethyl, cyclohexylacetamidomethyl, methylcyclohexanecarboxamidomethyl, (3-hydroxy-4,4,4-trichlorobutyramido)methyl, and phenylthioacetamidomethyl;

(w) ether is selected from ethylene ketal, and $C_{1-8}$alkyl ether optionally substituted with hydroxy, halo, $C_{1-8}$alkoxy, $C_{2-6}$alkenyl, or aryl;

(x) thioether is selected from: $C_{1-8}$alkylthio, phenylthio, and $C_{1-8}$alkylthio substituted with phenyl; and (y) substituted and unsubstituted aryl or heteroaryl ether is selected from thiophenoxy, biphenyloxy, acetamidophenoxy, (3-pyridyl)oxy, chlorophenyloxy, methylphenyloxy, phenoxy, hydroxyphenyloxy, methylsulfonylphenyloxy and pyrimidinyloxy.

In one embodiment of the instant invention are compounds of formula III wherein X is oxygen.

In one class of the compounds of this embodiment are compounds wherein Z is

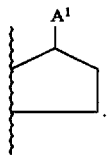

Exemplifying this class are:

(1) N-t-Butyl-4-oxa-5α-androst-1-en-3-one-17β-carboxamide, (2) 7β-Methyl-4-oxa-5α-cholest-1-en-3-one, (3) 17β-(2,5-bis(trifluoromethyl)phenylcarbamoyl)-4-oxa-5α-androst-1-en-3-one, (4) 17β-(2,3-bis(trifluoromethyl)phenylcarbamoyl)-4-oxa-5α-androst-1-en-3-one, (5) 17β-(2,4-bis(trifluoromethyl)phenylcarbamoyl)-4-oxa-5α-androst-1-en-3-one, (6) 17β-(2,6-bis(trifluoromethyl)phenylcarbamoyl)-4-oxa-5α-androst-1-en-3-one, (7) 17β-(N-tert-amylcarbamoyl)-4-oxa-5α-androst-1-en-3-one, (8) 17β-(N-tert-hexylcarbamoyl)-4-oxa-5α-androst-1-en-3-one, (9) 17β-(N-isobutylcarbamoyl)-4-oxa-5α-androst-1-en-3-one,

(10) 17β-(N-tert-octylcarbamoyl)-4-oxa-5α-androst-1-en-3-one,

(11) 17β-(N-1,1-diethylbutylcarbamoyl)-4-oxa-5α-androst-1-en-3-one,

(12) 17β-(N-neopentylcarbamoyl)-4-oxa-5α-androst-1-en-3-one,

(13) 17β-(N-2-adamantylcarbamoyl)-4-oxa-5α-androst-1-en-3-one,

(14) 17β-(N-1-adamantylcarbamoyl)-4-oxa-5α-androst-1-en-3-one,

(15) 17β-(N-2-norbornylcarbamoyl)-4-oxa-5α-androst-1-en-3-one,

(16) 17β-(N-1-norbornylcarbamoyl)-4-oxa-5α-androst-1-en-3-one,

(17) 17β-(N-phenylcarbamoyl)-4-oxa-5α-androst-1-en-3-one,

(18) 17β-(N-benzylcarbamoyl)-4-oxa-5α-androst-1-en-3-one,

(19) 17β-(2,3-bis(trifluoromethyl)phenylcarbamoyl)-7β-methyl-4-oxa-5α-androst-1-en-3-one,

(20) 17β-(2,4-bis(trifluoromethyl)phenylcarbamoyl)-7β-methyl-4-oxa-5α-androst-1-en-3-one,

(21) 17β-(2,6-bis(trifluoromethyl)phenylcarbamoyl)-7β-methyl-4-oxa-5α-androst-1-en-3-one,

(22) 17β-(N-n-octylcarbamoyl)-4-methyl-4-oxa-5α-androst-1-en-3-one,

(23) 17β-(1-methoxyethyl)-7β-methyl-4-oxa-5α-androst-1-en-3-one,

(24) 17β-(isopropyl)-7β-methyl-4-oxa-5α-androst-1-en-3-one,

(25) 17β-(4-methyl-phenoxy)-7β-methyl-4-oxa-5α-androst-1-en-3-one,

(26) 17β-(1-(3-chlorophenoxy)ethyl)-7β-methyl-4-oxa-5α-androst-1-en-3-one,

(27) 17β-(4-methylsulfonyl-phenoxy)-7β-methyl-4-oxa-5α-androst-1-en-3-one,

(28) 17β-(4-chlorophenoxy)-7β-methyl-4-oxa-5α-androst-1-en-3-one,

(29) 17β-(2-pyrimidinyloxy)-7β-methyl-4-oxa-5α-androst-1-en-3-one, and

(30) 17β-(2,5-bis(trifluoromethyl)phenylcarbamoyl)-7β-methyl-4-oxa-5α-androst-1-en-3-one.

In one subclass of this class are compounds wherein $R^1$ is hydrogen, $R^2$ is selected from H and $CH_3$, and $A^1$ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl)

carboxamide, N-(carbomethoxy)phenyl carboxamide, N-(methoxycarboxy) phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl) carboxamide, N-(diphenylmethyl)-carboxamide, N-t-butyl carboxamide, N-isopropyl carboxamide, 1-adamantyl carboxamide, 2-adamantyl carboxamide, and N-(substituted phenyl) carboxamides wherein the phenyl may be substituted with 1 to 2 substitutents selected from ethyl, methyl, trifluoromethyl or halo (F, Cl, Br, I).

Still further illustrating this subclass are compounds wherein carboxamide is —C(=O)NH—C(CH$_3$)$_3$, —C(=O)NH—C$_6$H$_5$ or —C(=O)NH—(2,5-trifluoromethylphenyl).

In one subclass of this class are compounds wherein R$^1$ is hydrogen, R$^2$ is selected from H and CH$_3$, the C5–C6 bond designated with a dotted line is a single bond, H$_a$ is present and represents hydrogen, and A$^1$ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy) phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl) carboxamide, N-(diphenylmethyl)-carboxamide, N-t-butyl carboxamide, N-isopropyl carboxamide, 1-adamantyl carboxamide, 2-adamantyl carboxamide, and N-(substituted phenyl) carboxamides wherein the phenyl may be substituted with 1 to 2 substitutents selected from ethyl, methyl, trifluoromethyl or halo (F, Cl, Br, I).

In one subclass of this class are compounds wherein R$^1$ is hydrogen, R$^2$ is selected from H and CH$_3$, the C5–C6 bond designated with a dotted line is a double bond, H$_a$ is absent, and A1 is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy) phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl) carboxamide, N-(diphenylmethyl)-carboxamide, N-t-butyl carboxamide, N-isopropyl carboxamide, 1-adamantyl carboxamide, 2-adamantyl carboxamide and N-(substituted phenyl) carboxamides, wherein the phenyl may be substituted with 1 to 2 substitutents selected from ethyl, methyl, trifluoromethyl or halo (F, Cl, Br, I).

In another subclass of this class are compounds wherein R$^1$ is CH$_3$, R$^2$ is selected from H and CH$_3$, and A$^1$ is a selected from: carboxamide, including substituted and unsubstituted anilide derivatives, and C$_{1-10}$ alkyl. Further illustrating this subclass are compounds wherein carboxamide is —C(=O)NH—C$_6$H$_5$ or —C(=O)NH-(2,5-trifluoromethylphenyl) and C$_{1-10}$alkyl is selected from isopropyl, isobutyl, 1,5-dimethylhexyl, and 5-methylhexyl.

In another class of the compounds of this embodiment are compounds wherein Z is

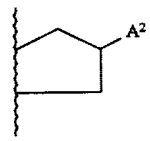

Exemplifying compounds of this class are:
(1) N-t-Butyl-4-oxa-5α-androst-1-en-3-one-16β-carboxamide,
(2) 16β-(1,5-dimethylhexyl)-7β-Methyl-4-oxa-5α-androst-1-en-3-one,
(3) 16β-(2,5-bis(trifluoromethyl)phenylcarbamoyl)-4-oxa-androst-1-en-3-one,
(4) 16β-(N-tert-amylcarbamoyl)-4-oxa-5α-androst-1-en-3-one,
(5) 16β-(N-tert-hexylcarbamoyl)-4-oxa-5α-androst-1-en-3-one,
(6) 16β-(N-isobutylcarbamoyl)-4-oxa-5α-androst-1-en-3-one,
(7) 16β-(N-tert-octylcarbamoyl)-4-oxa-5α-androst-1-en-3-one,
(8) 16β-(N-1,1-diethylbutylcarbamoyl)-4-oxa-5α-androst-1-en-3-one,
(9) 16β-(N-neopentylcarbamoyl)-4-oxa-5α-androst-1-en-3-one,
(10) 16β-(N-2-adamantylcarbamoyl)-4-oxa-5α-androst-1-en-3-one,
(11) 16β-N-1-adamantylcarbamoyl)-4-oxa-5α-androst-1-en-3-one,,
(12) 16β-(N-2-norbornylcarbamoyl)-4-oxa-5α-androst-1-en-3-one,
(13) 16β-(N-1-norbornylcarbamoyl)-4-oxa-5α-androst-1-en-3-one,
(14) 16β-(N-phenylcarbamoyl)-4-oxa-5α-androst-1-en-3-one,
(15) 16β-(N-benzylcarbamoyl)-4-oxa-5α-androst-1-en-3-one,
(16) 16β-(2,3-bis(trifluoromethyl)phenylcarbamoyl)-7β-methyl-4-oxa-5α-androst-1-en-3-one,
(17) 16β-(2,4-bis(trifluoromethyl)phenylcarbamoyl)-7β-methyl-4-oxa-5α-androst-1-en-3-one,
(18) 16β-(2,6-bis(trifluoromethyl)phenylcarbamoyl)-7β-methyl-4-oxa-5α-androst-1-en-3-one,
(19) 16β-(2,3-bis(trifluoromethyl)phenylcarbamoyl)-4-oxa-androst-1-en-3-one,
(20) 16β-(2,4-bis(trifluoromethyl)phenylcarbamoyl)-4-oxa-androst-1-en-3-one,
(21) 16β-(2,6-bis(trifluoromethyl)phenylcarbamoyl)-4-oxa-androst-1-en-3-one,
(22) 16β-(N-n-octylcarbamoyl)-4-methyl-4-oxa-5α-androst-1-en-3-one,
(23) 16β-(1-methoxyethyl)-7β-methyl-4-oxa-5α-androst-1-en-3-one,
(24) 16β-(isopropyl)-7β-methyl-4-oxa-5α-androst-1-en-3-one,
(25) 16β-(4-methyl-phenoxy)-7p-methyl-4-oxa-5α-androst-1-en-3-one,
(26) 16β-(1-(3-chlorophenoxy)ethyl)-7β-methyl-4-oxa-5α-androst-1-en-3-one,
(27) 16β-(4-methylsulfonyl-phenoxy)-7β-methyl-4-oxa-5α-androst-1-en-3-one,
(28) 16β-(4-chlorophenoxy)-7β-methyl-4-oxa-5α-androst-1-en-3-one,

(29) 16β-(2-pyrimidinyloxy)-7β-methyl-4-oxa-5α-androst-1-en-3-one, and

(30) 16β-(2,5-bis(trifluoromethyl)phenylcarbamoyl)-7β-methyl-4-oxa-5α-androst-1-en-3-one.

In one subclass of this class, $R^1$ is H or $CH_3$, $R^2$ is selected from H and $CH_3$, and $A^2$ is selected from: substituted and unsubstituted aryl or heteroaryl ether. Further illustrating this subclass are the compounds wherein substituted and unsubstituted aryl or heteroaryl ether is selected from thiophenoxy, biphenyloxy, acetamidophenoxy, (3-pyridyl) oxy, chlorophenyloxy, methylphenyloxy, phenoxy, hydroxyphenyloxy, methylsulfonylphenyloxy and pyrimidinyloxy. Still further illustrating the compounds of the present invention are compounds wherein substituted or unsubstituted aryl or heteroaryl ether is selected from 4-methyl-phenoxy, 4-chlorophenoxy, and 2-pyrimidinyloxy.

In another embodiment of the compounds of structural formula (III) are compounds of formula I wherein X is sulfur.

In one class of the compounds of this embodiment are compounds wherein Z is

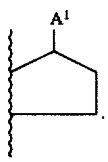

Exemplifying compounds of this class are:
(1) N-t-Butyl-4-thia-5α-androst-1-en-3-one-17β-carboxamide,
(2) 7β-Methyl-4-thia-5α-cholest-1-en-3-one,
(3) 17β-(2,5-bis(trifluoromethyl)phenylcarbamoyl)-4-thia-5α-androst-1-en-3-one,
(4) 17β-(2,3-bis(trifluoromethyl)phenylcarbamoyl)-4-thia-5α-androst-1-en-3-one,
(5) 17β-(2,4-bis(trifluoromethyl)phenylcarbamoyl)-4-thia-5α-androst-1-en-3-one,
(6) 17β-(2,6-bis(trifluoromethyl)phenylcarbamoyl)-4-thia-5α-androst-1-en-3-one,
(7) 17β-(N-tert-amylcarbamoyl)-4-thia-5α-androst-1-en-3-one,
(8) 17β-(N-tert-hexylcarbamoyl)-4-thia-5α-androst-1-en-3-one,
(9) 17β-(N-isobutylcarbamoyl)-4-thia-5α-androst-1-en-3-one,
(10) 17β-(N-tert-octylcarbamoyl)-4-thia-5α-androst-1-en-3-one,
(11) 17β-(N-1,1-diethylbutylcarbamoyl)-4-thia-5α-androst-1-en-3-one,
(12) 17β-(N-neopentylcarbamoyl)-4-thia-5α-androst-1-en-3-one,
(13) 17β-(N-2-adamantylcarbamoyl)-4-thia-5α-androst-1-en-3-one,
(14) 17β-(N-1-adamantylcarbamoyl)-4-thia-5α-androst-1-en-3-one,
(15) 17β-(N-2-norbornylcarbamoyl)-4-thia-5α-androst-1-en-3-one,
(16) 17β-(N-1-norbornylcarbamoyl)-4-thia-5α-androst-1-en-3-one,
(17) 17β-(N-phenylcarbamoyl)-4-thia-5α-androst-1-en-3-one,
(18) 17β-(N-benzylcarbamoyl)-4-thia-5α-androst-1-en-3-one,
(19) 17β-(2,3-bis(trifluoromethyl)phenylcarbamoyl)-7β-methyl-4-thia-5α-androst-1-en-3-one,
(20) 17β-(2,4-bis(trifluoromethyl)phenylcarbamoyl)-7β-methyl-4-thia-5α-androst-1-en-3-one,
(21) 17β-(2,6-bis(trifluoromethyl)phenylcarbamoyl)-7β-methyl-4-thia-5α-androst-1-en-3-one,
(22) 17β-(N-n-octylcarbamoyl)-4-methyl-4-thia-5α-androst-1-en-3-one,
(23) 17β-(1-methoxyethyl)-7β-methyl-4-thia-5α-androst-1-en-3-one,
(24) 17β-(isopropyl)-7β-methyl-4-thia-5α-androst-1-en-3-one,
(25) 17β-(4-methyl-phenoxy)-7β-methyl-4-thia-5α-androst-1-en-3-one,
(26) 17β-(1-(3-chlorophenoxy)ethyl)-7α-methyl-4-thia-5α-androst-1-en-3-one,
(27) 17β-(4-methylsulfonyl-phenoxy)-7β-methyl-4-thia-5α-androst-1-en-3-one,
(28) 17β-(4-chlorophenoxy)-7β-methyl-4-thia-5α-androst-1-en-3-one,
(29) 17β-(2-pyrimidinyloxy)-7β-methyl-4-thia-5α-androst-1-en-3-one, and
(30) 17β-(2,5-bis(trifluoromethyl)phenylcarbamoyl)-7β-methyl-4-thia-5α-androst-1-en-3-one.

In one subclass of this class are compounds wherein $R^1$ is hydrogen, $R^2$ is selected from H and $CH_3$, and $A^1$ is selected from: carboxamide, including substituted and unsubstituted anilide derivatives.

Further illustrating this subclass are compounds wherein carboxamide is selected from: N,N-diisopropyl carboxamide, N-t-butyl carboxamide, N-t-octyl carboxamide, N-n-octyl carboxamide, N-(hydroxyphenyl) carboxamide, N-phenylcarboxamide, N-(aminophenyl) carboxamide, N-(carbomethoxy)phenyl carboxamide, N-(methoxycarboxy) phenyl carboxamide, N-acetamidophenyl-N-acetyl-carboxamide, N-acetamidophenyl-carboxamide, N-pivalamidophenyl carboxamide, N-isobutyramidophenyl carboxamide, N-(methyl),N-(diphenylmethyl) carboxamide, N-(diphenylmethyl)-carboxamide, N-t-butyl carboxamide, N-isopropyl carboxamide, 1-adamantyl carboxamide, 2-adamantyl carboxamide, and N-(substituted phenyl) carboxamides wherein the phenyl may be substituted with 1 to 2 substitutents selected from ethyl, methyl, trifluoromethyl or halo (F, Cl, Br, I).

In another subclass of this class are compounds wherein $R^1$ is $CH_3$, $R^2$ is selected from H and $CH_3$, and $A^1$ is a selected from: carboxamide, including substituted and unsubstituted anilide derivatives, and $C_{1-10}$ alkyl. Further illustrating this subclass are compounds wherein carboxamide is —C(=O)NH—$C_6H_5$ or —C(=O)NH-(2,5-trifluoromethylphenyl) and $C_{1-10}$alkyl is selected from isopropyl, isobutyl, 1,5-dimethylhexyl, and 5-methylhexyl.

In another class of the compounds of this embodiment are compounds wherein Z is

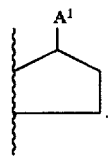

Exemplifying compounds of this class are:
(1) N-t-Butyl-4-thia-5α-androst-1-en-3-one-16β-carboxamide,
(2) 16β-(1,5-dimethylhexyl)-7β-Methyl-4-thia-5α-androst-1-en-3-one,
(3) 16β-(2,5-bis(trifluoromethyl)phenylcarbamoyl)-4-thia-androst-1-en-3-one, (4) 16β-(N-tert-amylcarbamoyl)-4-thia-5α-androst-1-en-3-one,
(5) 16β-(N-tert-hexylcarbamoyl)-4-thia-5α-androst-1-en-3-one,
(6) 16β-(N-isobutylcarbamoyl)-4-thia-5α-androst-1-en-3-one,
(7) 16β-(N-tert-octylcarbamoyl)-4-thia-5α-androst-1-en-3-one,
(8) 16β-(N-1,1-diethylbutylcarbamoyl)-4-thia-5α-androst-1-en-3-one,
(9) 16β-(N-neopentylcarbamoyl)-4-thia-5α-androst-1-en-3-one,
(10) 16β-(N-2-adamantylcarbamoyl)-4-thia-5α-androst-1-en-3-one,
(11) 16β-(N-1-adamantylcarbamoyl)-4-thia-5α-androst-1-en-3-one,
(12) 16β-(N-2-norbornylcarbamoyl)-4-thia-5α-androst-1-en-3-one,
(13) 16β-(N-1-norbornylcarbamoyl)-4-thia-5α-androst-1-en-3-one,
(14) 16β-(N-phenylcarbamoyl)-4-thia-5α-androst-1-en-3-one,
(15) 16β-(N-benzylcarbamoyl)-4-thia-5α-androst-1-en-3-one,
(16) 16β-(2,3-bis(trifluoromethyl)phenylcarbamoyl)-7β-methyl-4-thia-5α-androst-1-en-3-one,
(17) 16β-(2,4-bis(trifluoromethyl)phenylcarbamoyl)-7β-methyl-4-thia-5α-androst-1-en-3-one,
(18) 16β-(2,6-bis(trifluoromethyl)phenylcarbamoyl)-7β-methyl-4-thia-5α-androst-1-en-3-one,
(19) 16β-(2,3-bis(trifluoromethyl)phenylcarbamoyl)-4-thia-androst-1-en-3-one,
(20) 16β-(2,4-bis(trifluoromethyl)phenylcarbamoyl)-4-thia-androst-1-en-3-one,
(21) 16β-(2,6-bis(trifluoromethyl)phenylcarbamoyl)-4-thia-androst-1-en-3-one,
(22) 16β-(N-n-octylcarbamoyl)-4-methyl-4-thia-5α-androst-1-en-3-one,
(23) 16β-(1-methoxyethyl)-7β-methyl-4-thia-5α-androst-1-en-3-one,
(24) 16β-(isopropyl)-7β-methyl-4-thia-5α-androst-1-en-3-one,
(25) 16β-(4-methyl-phenoxy)-7β-methyl-4-thia-5α-androst-1-en-3-one,
(26) 16β-(1-(3-chlorophenoxy)ethyl)-7β-methyl-4-thia-5α-androst-1-en-3-one,
(27) 16β-(4-methylsulfonyl-phenoxy)-7β-methyl-4-thia-5α-androst-1-en-3-one,
(28) 16β-(4-chlorophenoxy)-7β-methyl-4-thia-5α-androst-1-en-3-one,
(29) 16β-(2-pyrimidinyloxy)-7β-methyl-4-thia-5α-androst-1-en-3-one, and
(30) 16β-(2,5-bis(trifluoromethyl)phenylcarbamoyl)-7β-methyl-4-thia-5α-androst-1-en-3-one.

In a subclass of this class, $R^1$ is H or $CH_3$, $R^2$ is selected from H and $CH_3$, and $A^2$ is selected from: substituted and unsubstituted aryl or heteroaryl ether. Further illustrating this subclass are the compounds wherein substituted and unsubstituted aryl or heteroaryl ether is selected from thiophenoxy, biphenyloxy, acetamidophenoxy, (3-pyridyl)oxy, chlorophenoxy, methylphenyloxy, phenoxy, hydroxyphenyloxy, methylsulfonylphenyloxy and pyrimidinyloxy. Still further illustrating the compounds of the present invention are compounds wherein substituted or unsubstituted aryl or heteroaryl ether is selected from 4-methyl-phenoxy, 4-chlorophenoxy, and 2-pyrimidinyloxy.

When any variable (e.g., aryl, heterocycle, $R^1$, etc.) occurs more than one time in any constituent or in formula I, its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), secbutyl (s-Bu), tertbutyl (t-Bu), isopentane, isohexane, etc. "Alkyloxy" (or "alkoxy") represents an alkyl group having the indicated number of carbon atoms attached through an oxygen bridge, e.g., methoxy, ethoxy, propyloxy, isopropoxy, n-butoxy, iso-butoxy, sec-butoxy, t-butoxy and the like.

The term "aryl" includes phenyl and naphthyl. Preferably, aryl is phenyl.

Heteroaryl is selected from piperidinyl, piperizinyl, pyrrolidinyl, pyrrolyl, furanyl, thienyl, pyridyl, pyrimidinyl, indolyl and benzofuranyl.

Heterocyclic rings may be attached to structural formula I at any heteroatom (N, O or S) or carbon atom in the ring which results in the creation of a stable, uncharged structure.

Hydroxy and amino protecting groups are known to those of ordinary skill in the art, and any such groups may be used. For example, acetate, benzoate, ether and silyl protecting groups are suitable hydroxy protecting groups. Standard silyl protecting groups have the general formula —Si(Xa)$_3$, wherein each Xa group is independently an alkyl or aryl group, and include, e.g. trimethylsilyl, tri-ethylsilyl, tri-i-propylsilyl, triphenylsilyl as well as t-butyl-di-(Xb)-silyl where Xb is methyl, ethyl, i-propyl or phenyl (Ph). Standard amino protecting groups have the general formula —C(O)—Xc, wherein Xc is alkyl, aryl, O-alkyl or O-aryl, and include, e.g. N-t-butoxycarbonyl. See also *Protective Groups in Organic Synthesis*, T. W. Green et al. (John Wiley and Sons, 1991) for descriptions of protecting groups. The 4-oxa compounds of this invention can be prepared as shown in Scheme 2.

SCHEME 2:

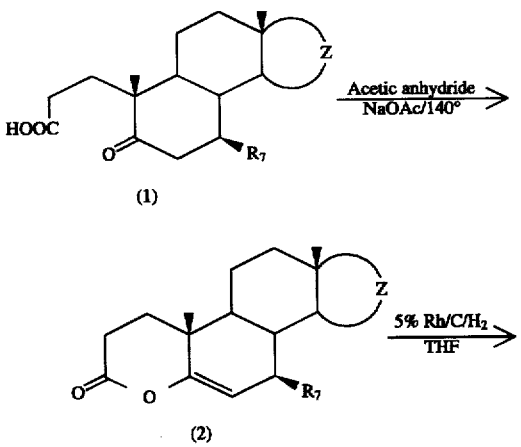

-continued
SCHEME 2:

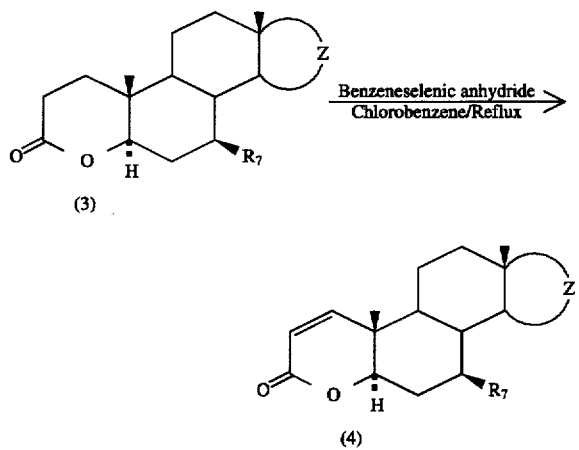

Scheme 2 outlines the synthesis of the novel oxasteroids of the present invention. The appropriately substituted seco-acid may be prepared by methods known in the art. PCT publication WO 95/11254 describes procedures for the synthesis of compounds having various substituents at the 16-position of the azasteroid. Starting with a 3-keto-delta4-17-one precursor and following the procedures of WO 95/11254, the appropriate $A^2$ substitution may be obtained. To obtain the appropriate $A^1$ substitution, the procedures of the following publications are followed starting with a 3-keto-delta4-17-one precursor: for ether or thioether WO 93/23040; for anilide WO 94/07861, EP 0 663 924; for unsubstituted, monosubstituted or disubstituted amides WO 93/23038, WO 93/23051, WO 93/23420; and U.S. Pat. Nos. 4,220,775, 4,760,071, 4,845,104, 5,237,067, 5,091,380, 5,061,801, 5,215,894, for oxo U.S. Pat. Nos. 4,220,775, 4,377,584; for cyano U.S. Pat. No. 4,220,775; for tetrazoyl U.S. Pat. No. 4,220,775; for arylalkylcarbonlyoxy alkyl U.S. Pat. No. 4,377,584; for cycloalkylarylcarbonlyoxy alkyl U.S. Pat. No. 4,377,584; for benzoyloxyalkyl U.S. Pat. No. 4,377,584; for acyl, both substituted and unsubstituted, U.S. Pat. No. 5,049,562, U.S. Pat. No. 5,138,063, U.S. Pat. No. 5,151,429, U.S. Pat. No. 5,237,061, U.S. Pat. No. 5,120,742, U.S. 5,162,332, U.S. Pat. No. 5,061,802, U.S. Pat. No. 5,098,908, U.S. Pat. No. 5,196,411, U.S. 5,075,450, U.S. Pat. No. 5,061,803, U.S. Pat. No. 5,324,734; for thiobenzyl U.S. Pat. No. 5,151,430; for polyaroyl U.S. Pat. No. 5,162,322; for ester U.S. Pat. No. 5,091,534, WO 93/23041, WO 93/23040, for alkyl, either substituted or unsubstituted WO 93/23050, WO 93/23419, WO 93/23051; for urea, thiourea, carbamate or thiocarbamate W093/23048; for thioester WO 93/23041, WO 93/23040.

The appropriately 7,10,16, and 17-substituted 3-keto steroid is converted to the appropriately substituted seco-acid by methods known in the art, for example, the procedures described in Rasmusson, et al., J. Med. Chem. 1986, 29(11): 2298–2315.

The appropriate 7-βsubstitution may be obtained following the procedures for formation of a 7-βbond as described in U.S. Pat. Nos. 4,220,775, and 5,237,064.

Compounds wherein $R^2$ is H or $CH_2OR^3$ may be prepared starting with the appropriately C10 substituted seco-acid. These compounds may be made by procedures known in the art.

As shown in Scheme 2, the seco-acid (1) is treated with a dehydrating agent such as acetic anhydride, methyl ortho-formate, ethyl ortho-formate, in a nonpolar aprotic solvent such as toluene, xylene, dichloroethane, chlorobenzene and the like optionally in the presence of an acidic catalyst, such as PTSA (paratoluenesulfonic acid), or sodium acetate to form the $\Delta^5$-oxasteroid (2). Preferably, the seco-acid (1) is treated with acetic anhydride in acetic anhydride in the presence of sodium acetate at an elevated temperature, preferably at about 140° C. Hydrogenation of the double bond to form the oxasteroid (3) may be carried out in the presence of an appropriate catalyst such as Rh/C, Pd/C, etc., preferably Rh/C in a solvent such as tetrahydrofuran (THF) or ethyl acetate. This is followed by formation of the $\Delta^1$ double bond by treatment with, for example, dichloro-dicyanoquinone (DDQ), benzeneselenic anhydride in chlorobenzene, or other known methods, for example as described in U.S. Pat. Nos. 5,084,574 and 5,021,571, to form the $\Delta^1$-oxasteroid (4).

The 4-thia compounds of this invention can be prepared as shown in Scheme 3.

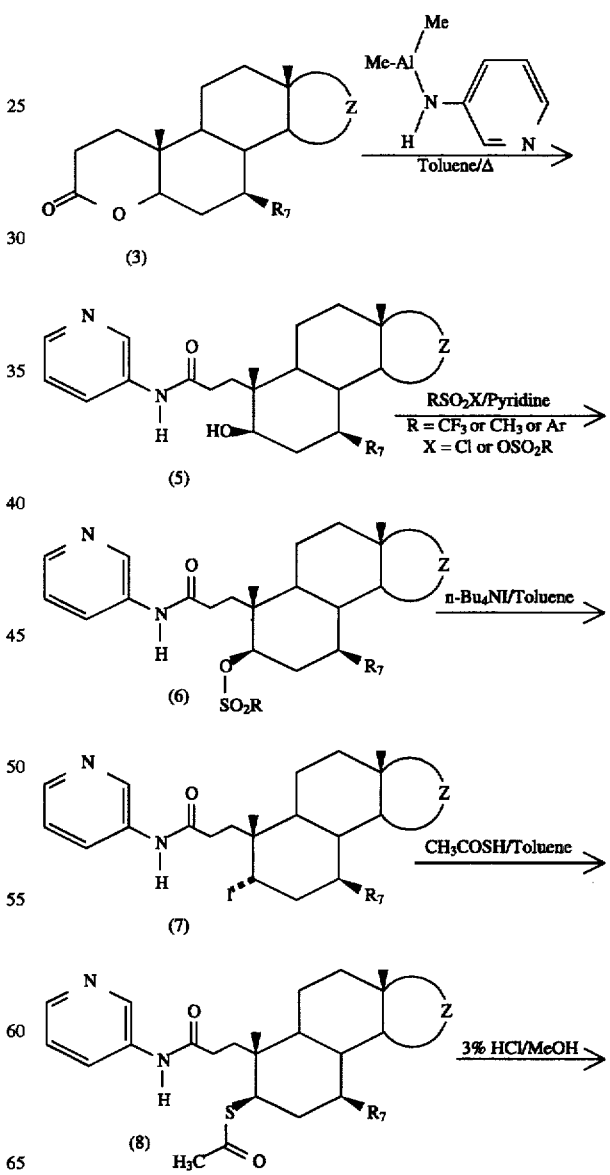

-continued

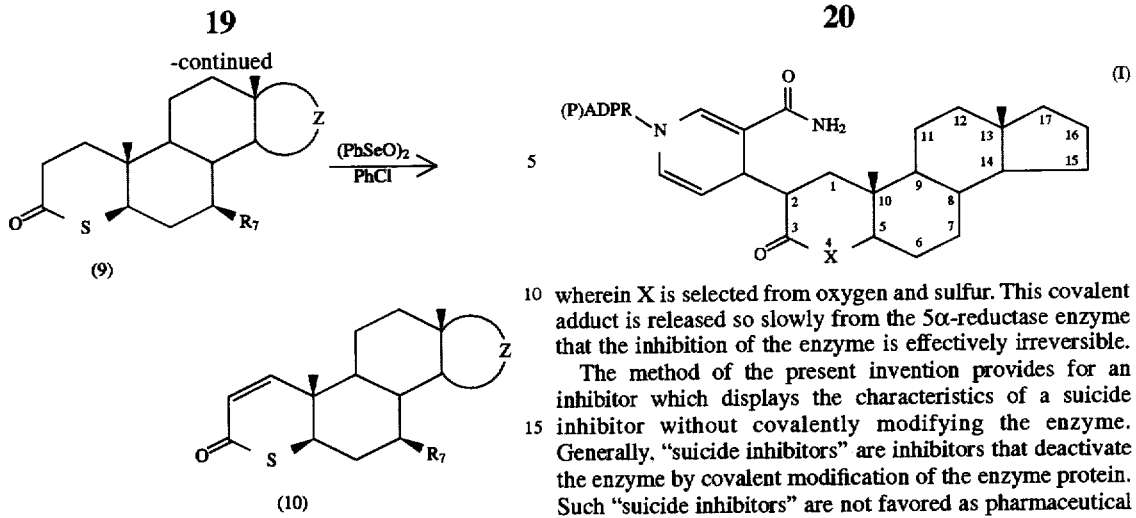

(9)

(10)

Starting with the 4-oxa-androstan-3-one appropriately substituted in the B and D-ring, obtained by following the procedures of Scheme 2 to obtain compound (3), the lactone is opened to form the hydroxamide (5). The lactone may be opened by various means such as treatment with dimethylalumino-3-aminopyridine (which may be prepared in situ by treating trimethyl aluminum with 3-amino pyridine), chlorobenzene or dichloroethane in a nonpolar, aprotic solvent such as toluene.

The hydroxamide (5) is treated with alkyl- or aryl sulfonyl chloride in a solvent such as methylene chloride, toluene or dichloroethane in the presence of a base such as pyridine, dimethylaminopyridine (DMAP), or N-methylpyrrolidine (NMP), to give the corresponding alkyl- or aryl sulfonate (6). The reaction of the alkyl- or aryl sulfonate with tetrabutylammonium iodide in a polar aprotic solvent such as toluene produces the corresponding iodide (7). The iodide is treated with thioacetic acid in a nonpolar solvent such as toluene or dichloroethane in the presence of cesium carbonate or other base such as potassium carbonate or sodium carbonate to give the thioacetate (8). The thioacetate (8) is hydrolyzed to form the thialactone (9), preferably by treatment with acid in a polar solvent such as methanol or ethanol, preferably by treatment with hydrochloric acid in methanol. The thialactone (9) may be dehydrogenated to form the $\Delta^1$-thiasteroid (10) as described above, preferably by treatment with benzeneselenic anhydride in chlorobenzene at reflux.

The 4-oxa and 4-thia steroids of the structural formula (III) include the 1,2-5,6 diene which may be prepared by treating the compound of structural formula (2) with benzeneselenic anhydride in chlorobenzene with refluxing to obtain the $\Delta^1,\Delta^5$-oxasteroid derivative. The corresponding thiasteroid derivative may be obtained by following the procedures of Scheme 2, starting with (2), the $\Delta^5$-oxasteroid.

More particularly, the present invention relates to a method for treating hyperandrogenic conditions in a human being in need of such treatment by irreversibly inhibiting the human 5α-reductase enzyme without covalently modifying the 5α-reductase enzyme. This method comprises the administration to the human in need of such treatment of a 3-oxo-4-oxa and 4-thiasteroid having a 1,2-double bond. The 3-oxo-4-oxa and 4-thiasteroid having a 1,2-double bond is selectively activated by 5α-reductase to produce the covalent adduct with the cofactor NADPH of structural formula (I).

wherein X is selected from oxygen and sulfur. This covalent adduct is released so slowly from the 5α-reductase enzyme that the inhibition of the enzyme is effectively irreversible.

The method of the present invention provides for an inhibitor which displays the characteristics of a suicide inhibitor without covalently modifying the enzyme. Generally, "suicide inhibitors" are inhibitors that deactivate the enzyme by covalent modification of the enzyme protein. Such "suicide inhibitors" are not favored as pharmaceutical agents because the covalently-modified enzyme may be recognized by the immune system of the treated organism as foreign matter and trigger an undesirable immunological response. The non-protein bound adduct of the present invention eliminates the possibility of such an undesirable immunological response.

The long-lived enzyme-bound 3-oxo-4-oxasteroid-NADP adduct and 3-oxo-4-thiasteroid NADP adduct of the present invention provides further advantages in clinical settings. The method of the present invention provides for sustained inhibition of 5α-reductase even when the dose regimen is interrupted and the levels of the 3-oxo-4-oxasteroid or 3-oxo-4-thiasteroid drug having a 1,2-double bond drop, as when the patient misses a dose. In this situation of interrupted dosing, 5α-reductase that had been inhibited cannot recover from the inhibition and additional drug is required to inhibit only the 5α-reductase that has been newly synthesized by the patient.

Hyperandrogenic conditions treatable by the method of the present invention include benign prostatic hyperplasia, androgenic alopecia, acne vulgaris, seborrhea, female hirsutism, prostatitis and prostatic carcinoma.

The 3-oxo-4-oxa and 4-thiasteroids having a 1,2-double bond useful in the present invention are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices may be administered systemically, by oral administration or by intravenous or intramuscular injection or topically.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carriers, and placing the mixture in gelatin capsules.

Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Topical preparations containing the active drug component can be admixed with a variety of carrier materials well known in the art, such as, e.g., alcohols, aloe vera gel, allantoin, glycerine, vitamin A and E oils, mineral oil, propylene glycol, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Advantageously, the active agent of the present invention may be administered in a single daily dose, or the total daily dosage may be administered in dividend doses of two, three or four times daily. The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the 3-oxo-4-oxa and 4-thiasteroid having a 1,2-double bond useful in the method of the present invention range from 0.001 to 100 mg per day, preferably 0.05 to 50 mg per day and as provided by the advantage of the present invention, doses inadvertently missed will not compromise the therapeutic efficacy. Most preferably, dosages range from 0.01 to 10 mg/day.

The $\Delta^1$-3-oxo-4-oxa and 4-thiasteroids of the present invention may be administered on a cyclical regimen. The details of the effective regimen depend on the particular $\Delta^1$-3-oxo-4-oxa and 4-thiasteroid administered. These cyclical regimens provide an advantage over classical drugs, i.e., pharmaceutically active agents that do not function as an irreversible inhibitor.

The $\Delta^1$-3-oxo-4-oxa and 4-thiasteroids of the present invention may be administered in the form of pharmaceutically acceptable salts. The term "pharmaceutically acceptable salt" is intended to include all acceptable salts such as hydrochloride, hydrobromide, acetate, panoate and the like which can be used as a dosage form for modifying the solubility or hydrolysis characteristics or can be used in sustained release or pro-drug formulations. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tanmate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formulae I, II and III, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

For the treatment of acne vulgaris, androgenic alopecia, male pattern baldness, seborrhea, female hirsutism, benign prostatic hyperplasia, prostatitis and the prevention and/or treatment of prostatic cancer, the compounds of the instant invention can be combined with a therapeutically effective amount of another 5α-reductase inhibitor, such as finasteride or episteride, or other 5α-reductase inhibitor compounds having type 2 activity, type 1 activity or dual activity for both isozymes, in a single oral, systemic, or parenteral pharmaceutical dosage formulation. Alternatively, a combined therapy can be employed wherein the compound of formula I and the other 5α-reductase inhibitor are administered in separate oral, systemic, or parenteral dosage formulations. Also, for the skin and scalp related disorders of acne vulgaris, androgenic alopecia, male pattern baldness, seborrhea, and female hirsutism, the compounds of the instant invention and another 5α-reductase inhibitor such as finasteride or episteride can be formulated for topical administration. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. Nos. 4,377,584 and 4,760,071 which describe dosages and formulations for 5α-reductase inhibitors.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. Therapy may further comprise the administration of a 5α-reductase type 2 inhibitor such as finasteride or episteride, or a 5α-reductase type 1 inhibitor, or a type 1 and type 2 dual inhibitor, in combination with a compound of the present invention and a potassium channel opener such as minoxidil. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. Nos. 4,596,812, 4,139,619 and WO 92/02225, published 20 Feb. 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g. an ester or amide derivative thereof, such as e.g., tretinoin or isotretinoin. Optionally, this combined therapy for acne vulgaris may further include a 5α-reductase type 2 inhibitor such as finasteride or episteride, or a 5α-reductase type 1 inhibitor, or a dual type 1 and type 2 inhibitory compound.

Also, for the treatment of benign prostatic hyperplasia, a combined therapy comprising a administration of a compound of formula I with a 5α-reductase type 2 inhibitor, such as e.g., finasteride, and an alpha-1 adrenergic receptor antagonist, such as e.g., terazosin, doxazosin, prazosin, bunazosin, indoramin or alfuzosin, may be employed. More particularly, the combined therapy can comprise administering a compound of formula I with a 5α-reductase type 2 inhibitor, such as e.g., finasteride, and an alpha-$1_a$ adrenergic receptor antagonist (formerly called an alpha-$1_c$ adrenergic receptor antagonist). Compounds which are useful as alpha-$1_a$ adrenergic receptor antagonists can be identified according to procedures known to those of ordinary skill in the art, for example, as described in PCT/US93/09187 (WO94/08040, published Apr. 14, 1994); PCT/US94/03852 (WO 94/22829, published Oct. 13, 1994); PCT/US94/10162 (WO 95/07075, published Mar. 16, 1995), and U.S. Pat. No. 5,403,847.

Also, for the treatment of acne vulgaris, androgenic alopecia, seborrhea, female hirsutism, benign prostatic hyperplasia, prostatitis and the prevention and/or treatment of prostatic cancer, a combined therapy can be used by administering a therapeutically effective amount of a compound of formula I with a therapeutically effective amount of an anti-androgen, such as, e.g., flutamide, spironolactone or casodex.

For combination treatment with more than one active agent, where the active agents are in separate dosage formulations, the active agents can be administered concomitantly, or they each can be administered at separately staggered times.

Biological Assays

The standard assay contains 100 pM membrane-bound enzyme suspended in a solution of 25 nM [$^3$H]testosterone (139,000 dpm, carrier free) and 500 µM NADPH in a buffer consisting of 0.1M MOPS, 1 mM EDTA, and 0.1% BSA, at pH 7.20 and 37° C., in a total volume of 100 µL. Ethanol is included at 1% final concentration as the vehicle for introduction of inhibitors. The rate of production of [$^3$H] dihydrotestosterone is approximately constant for up to 2 hours or 10% consumption of substrate. A unit of enzyme activity was defined as 1 pmol product/min, and is equal to 444 fmol enzyme under these conditions.

Alternatively, measurements may be conducted under conditions that have more traditionally been employed for this enzyme at pH 5.50 and 37° C.

After quenching the reactions with an equal volume, or more, of water containing 1% trifluoroacetic acid, the [$^3$H] dihydrotestosterone is isolated by direct injection onto a reverse phase C-18 column (Vydac, 4.6×250 mm, 300 Å, 5 micron), which is run in an isocratic system of 40% water (containing 0.1% trifluoroacetic acid) and 60% methanol at 1 mL/min. When tissue extracts are the source of enzyme, the quenched reactions are clarified by centrifugation at 10,000×g before analysis. Retention times are ~13 min for testosterone and ~20 min for dihydrotestosterone. The effluent containing the [$^3$H]dihydrotestosterone peak (6 mL) is collected in a liquid scintillation vial and counted with AQUASOL 2 (14 mL, New England Nuclear) with an efficiency of 0.309. The assay is completely automated using a SUN SPARKSTATION 2 computer interfaced to a ZYMARK robot and ancillary equipment.

Enzyme Sources

The native human enzyme was from prostate (type 2) or scalp (type 1) tissue, and the recombinant human enzymes were produced by the baculovirus expression system of Andersson, et al. (Chan, H. K., Geissler, W. M., Andersson, S., Sex Hormones and Antihormones in Endocrine Dependent Pathology: Basic and Clinical Aspects, M. Motta and M. Serio, eds., Elsevier Science 1994). A comparable baculovirus expression system also has been described recently by Tian et al., Biochemistry, 33: 2291–2296 (1994). Enzyme concentrations were determined by titration with finasteride, or [$^3$H]finasteride, or from catalytic activity using kcat and Km values.

Under the standard assay conditions, the $K_m$ of the baculovirus-expressed type 2 enzyme for testosterone was found to be 24.6±0.7 nM at pH 7.2 and 37° C. This $K_m$ value agrees with that determined by Faller, et al. Biochemistry 32: 5705–5710 (1993) for the native human prostate enzyme at neutral pH ($K_m$=20±3 nM). The $K_m$ for NADPH was found to be ~1 μM under the assay conditions and 10×$K_m$ testosterone. The turnover number was $k_{cat}$=0.075±0.006 s$^{-1}$ at pH 7.2 and 37° C., as determined by titration with finasteride. From these kinetic constants, $k_{cat}/K_m$= 2.99±0.32×10$^6$M$^{-1}$ s$^{-1}$. The $K_m$ for the type 1 5α-reductase was 7 μM, and the kcat for the type 1 enzyme was 1.4 sec$^{-1}$. The molecular weight was taken to be about 30,000 in estimating enzyme purity.

Inhibition studies

Compounds were dissolved in 100% ethanol. The compound to be tested was pre-incubated with the enzyme (either 5α-reductase type 1 or 2) prior to initiation by addition of substrate testosterone. IC$_{50}$ values represent the concentration of inhibitor required to decrease enzyme conversion of testosterone to dihydrotestosterone by 50% of the control. IC$_{50}$ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 1 inhibitor is a compound that shows inhibition of the 5α-reductase 1 isozyme in the above-described assay, having an IC$_{50}$ value of about or under 100 nM.

A compound referred to herein as a 5α-reductase 2 inhibitor is a compound that shows inhibition of the 5α-reductase 2 isozyme in the above-described assay, having an IC$_{50}$ value of about or under 100 nM.

EXAMPLE 1

Determination of Rate Constant for Formation of The Enzyme: 17β-(N-diethyl)carbamoyl-4-oxa-5α-androst-1-en-3-one Complex Progress curves of DHT formation were used to follow the time course for inhibition by (17β-(N-diethyl) carbamoyl-4-oxa-5α-androst-1-en-3-one (L-682,299). For this example, baculovirus expressed type 2 5α-reductase was incubated with 25 nM [$^3$H]testosterone and 100 μM NADPH with or without 20 nM inhibitor in a buffer composed of 0.1M MOPS, 0.1% BSA, and 1 mM EDTA at pH 7.2 and 37° C. Aliquots were withdrawn and testosterone separated from DHT by reverse phase HPLC (C18 column 1 mL/min, 60% methanol, 0.1% TFA. T elutes at about 13 minutes, DHT at about 20 minutes. The $^3$H in the T and DHT fractions was determined by scintillation counting using an in line radioflow detector. Alternatively, fractions may be collected and the samples counted on a scintillation counter. With this 4-oxasteroid, the inhibition developed slowly with time and resulted in total inhibition of the enzyme at infite time. The time courses were fit to an integrated first-order rate equation (Equation 1), where A is product concentration, $v_o$ is the initial velocity, $v_s$ is the infinite-time velocity, and $k_{obs}$ is the first-order rate constant for progression of the enzyme between the two equilibrium states. This 4-oxasteroid was found to bind to the type 2 isozyme with a second-order rate constant of 5.60×10$^4$M$^{-1}$ s$^{-1}$. The velocity at infinite-time was essentially zero. Consequently, the inhibitor was determined to be extremely potent, having a Ki<<100 pM. (Ki=$k_{off}/k_{on}$).

$$A=v_s t+(v_o-v_s)(1-e^{-k_{obs}t})/k_{obs}+Ao \qquad \text{Equation 1}$$

EXAMPLE 2

Determination of Rate Constant for Formation of The Enzyme: Inhibitor Complex

Similar studies may be conducted as described in Example 1 with other 4-oxa or 4-thia steroids having a 1,2 double bond using either the type 1 or type 2 5α-reductase. The enzyme used in these experiments may be either from native sources (human scalp or prostate) or recombinantly produced (baculovirus-expressed, COS cell expressed).

EXAMPLE 3

Determination of The Rate of Release of The Inhibitor From The Enzyme

Starting with radioactively-labeled inhibitor such as [1,2-$^3$H]-inhibitor, which may be prepared according to procedures well known in the art, such as tritium reduction of the $\Delta^1$ precursor with tritium gas and a Pd/C catalyst as described by Liang et al. Endocrinology (1983) 112: 1430, the loss of the $^3$H from the enzyme could be used to determine the rate of release of the inhibitor from the type 1 or 2 5α-reductase. Either native or recombinantly-expressed 5α-reductase may be incubated with the [1,2-$^3$H]-inihibitor and NADPH. If necessary, excess $^3$H-inhibitor not bound to the enzyme may be removed by dialysis prior to determination of the radioactivity bound to the enzyme. The concentrations of bound and free radioactivity could be determined by ultrafiltration on 10,000 Da cutoff membranes (AMICON, Centricon-10), which would be centrifuged for several hours at 4° C. Typically, 100 μL samples would be diluted to 1 mL with water before ultrafiltration, and the 3H in the total solution and the filtrate determined by scintillation counting.

EXAMPLE 4

Evidence For Reduction of The Inhibitor

Type 1 or 2 5α-reductase (native or recombinantly produced) could be incubated with radiolabeled inhibitor and NADPH to produce the enzyme:inhibitor complex. Excess inhibitor could be removed by dialysis of the enzyme solution. Release of the reduced inhibitor from the enzyme:inhibitor complex can be accomplished by heat denaturation in a boiling water bath for 90 min. The denatured protein can be removed by centrifugation or ultrafiltration through a 10,000 Da cutoff membrane (AMICON, YM-10). The identity of the radioactive species could be determine d by reverse phase high pressure liquid chromatography, for example a $C_8$ column with a linear gradient of 1 mL/minute of water to 100% methanol over 30 minutes.

The material released from the enzyme will no longer comigrate with the parent $\Delta^1$-4-oxa or 4-thia inhibitor. This process could be scaled up to produce sufficient material for structure identification by mass spectrometry.

EXAMPLE 5

Evidence For Noncovalent Binding to The Enzyme

Starting with radiolabeled inhibitor such as [1,2-$^3$H] inhibitor, enzyme:inhibitor complex could be prepared by incubation of the labeled inhibitor, NADPH and recombinantly produced or native type 1 or 2 5α-reductase. Denaturation of the enzyme-inhibitor complex with an equal volume of 95% ethanol containing 20 mM ammonium bicarbonate, pH 9.0 would liberate the NADP-inhibitor covalent adduct (structure 1). The suspension should be stirred for 30 min at room temperature, then centrifuged at 10,000×g for 45 min to remove the insoluble matter. Alternatively, 6M guanidine:HCl or other organic solvents could be used to liberate the adduct. After release of the adduct from the enzyme, all solutions should contain ammonium bicarbonate adjusted to pH 9 with ammonium hydroxide to buffer the free adduct. The radiolabeled adduct could be purified by using anion exchange chromatography such as a Pharmacia Mono Q anion exchange column $HCO_3^-$ form equilibrated to 0.01M ammonium bicarbonate, pH 9, and 50% methanol.

EXAMPLE 6

Preparation of N-t-Butyl-4-oxa-5α-androst-1-en-3-one-17β-carboxamide

Step 1: Benzotriazol-1'-yl-3-oxo-androst-4-ene-17β-carboxamide.

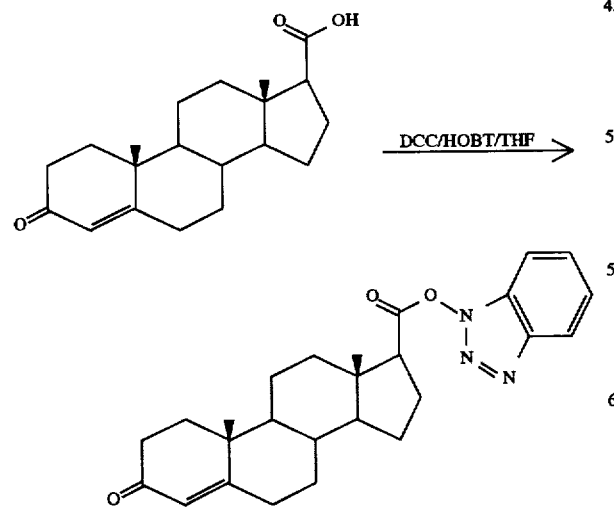

To a solution of steroid acid (4g, 12.65 mmol) in methylene chloride was added DCC (2.75 g, 13.3 mmol) and 1-hydroxybenzotriazole (HOBT, 2.75 g, 19.1 mmol). After stirring the reaction mixture for overnight, the solid was filtered, dried and used as such for further reactions.

Step 2: N-t-Butyl-3-oxo-androst-4-ene-17β-carboxamide.

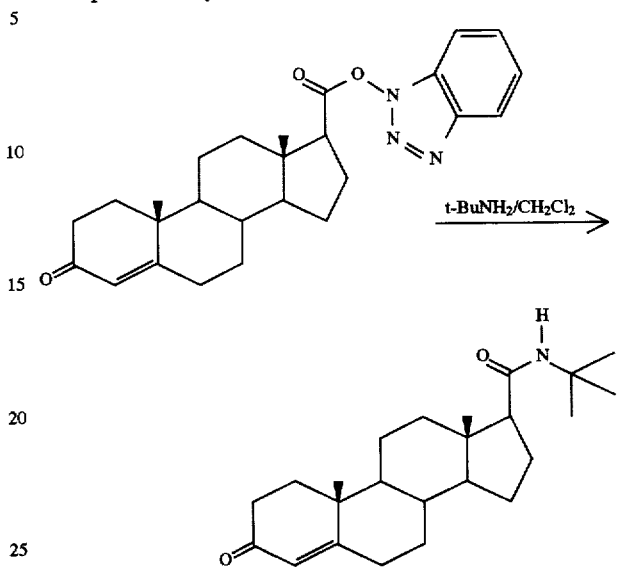

To a solution of benzotriazol-1'-yl-3-oxo-androst-4-ene-17β-carboxamide (1.5 g, 3.46 mmol) in methylene chloride was added t-butyl amine (454 µl, 4.33 mmol). After stirring the reaction mixture for overnight, the reaction mixture was concentrated, purified by chromatography over silica gel (2.5% acetone/methylene chloride). Mass spec. M$^+$ 372(m+1, observed).

Step 3: N-t-Butyl-5-oxo-3,5-secoandrostan-3-oic-17β-carboxamide.

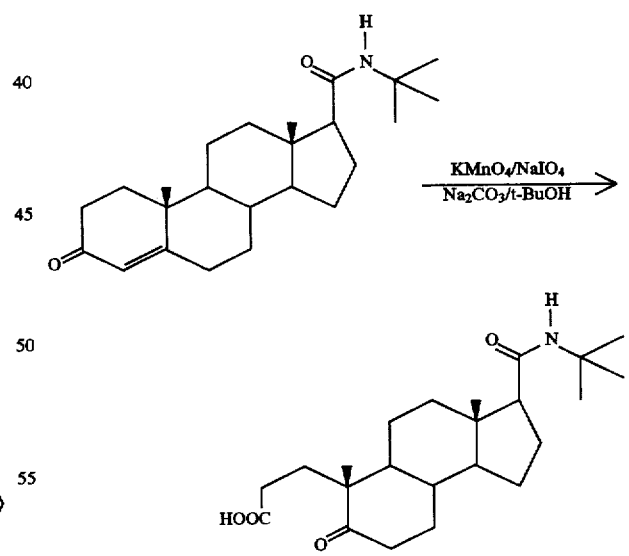

To a solution of N-t-butyl-3-oxo-androst-4-ene-17β-carboxamide (550 mg, 1.48 mmol) in t-butanol (10 mL) was added sodium carbonate (172 mg, 1.63 mmol, in 1 mL of $H_2O$). The reaction mixture was heated to 80° and a solution of $NaIO_4$ (1.58 g, 7.4 mmol) and $KMnO_4$ (11.7 mg, 0.074 mmol) in $H_2O$ (10 mL) was added dropwise in ~10 minutes. After stirring the reaction mixture for 2 hrs, the mixture was cooled to room temperature and acidified to pH 2. The reaction mixture was concentrated, extracted with ethyl acetate, organic layer was dried and concentrated to give pure product. Mass spec. M+392(m+1, observed).

Step 4: N-t-Butyl-4-oxa-androst-5-en-3-one-17β-carboxamide.

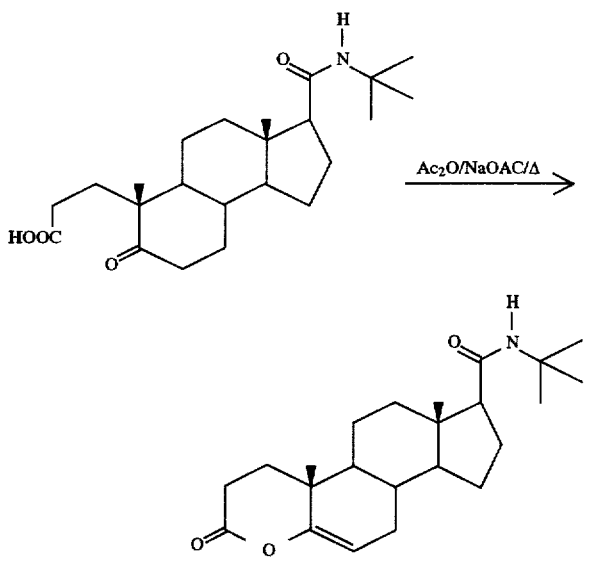

To a solution of N-t-butyl-5-oxo-3,5-secoandrostan-3-oic-17β-carboxamide (550 mg, 1.4 mmol) in acetic anhydride (25 mL) was added sodium acetate (1.91 g, 14 mmol). After stirring the reaction mixture at reflux temperature for 4 hrs, the acetic anhydride was removed under vacuum and residue partitioned between ethyl acetate and water. The organic layer was washed with brine, dried, concentrated and purified by prep. tlc (5% acetone/methylene chloride). Mass spec. M+ 374(m+1, observed).

Step 5: N-t-Butyl-4-oxa-5α-androstan-3-one-17β-carboxamide.

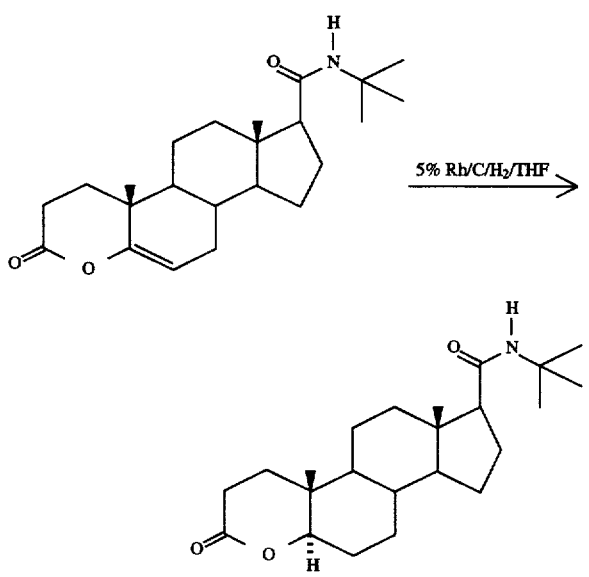

To a solution of N-t-butyl-4-oxa-androst-5-en-3-one-17β-carboxamide (410 mg, 1.099 mmol) in THF (20 mL) was added 5% Rh/C(410 mg). After stirring the reaction mixture under H₂ atmosphere for overnight, the mixture was flushed with N₂, filtered and concentrated. The residue was purified by prep. tlc (5% acetone/CH₂Cl2). Mass spec. M+376(m+1, observed).

Step 6: N-t-Butyl-4-oxa-5α-androst-1-en-3-one-17β-carboxamide.

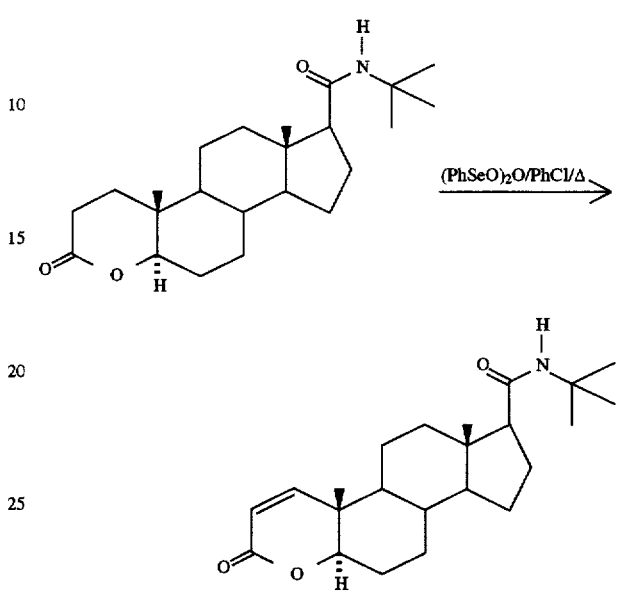

To a solution of N-t-butyl-4-oxa-5α-androstan-3-one-17β-carboxamide (100 mg, 0.27 mmol) in chlorobenzene was added benzeneseleninic anhydride (177 mg, 0.49 mmol). After stirring the reaction mixture at reflux temperature for overnight, the reaction mixture was diluted with ethyl acetate, washed with brine, dried and concentrated. The residue was purified by prep. tlc (5% acetone/CH₂Cl₂). Mass spec. M+374(m+1, observed).

EXAMPLE 7

Preparation of 7β-Methyl-4-oxa-5α-Cholest-1-en-3-one

Step 1: 7β-Methyl-4-oxa-Cholest-5-en-3-one

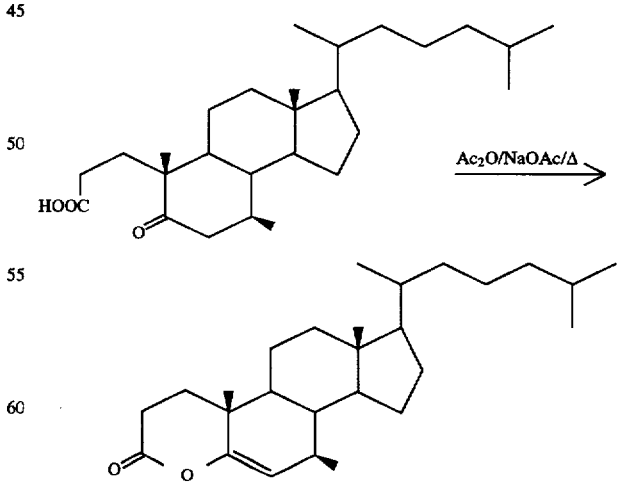

To a solution of 7β-methyl-5-oxo-3,5-sec-cholestan-3-oic (5 g, 12.3 mmol) in acetic anhydride (250 mL) was added sodium acetate ( 16.9 g, 124 mmol). After stirring the reaction mixture at reflux temperature for 4 hrs. the acetic anhydride was removed under vacuum and residue partitioned between ethyl acetate and water. The organic layer was washed with brine, dried, concentrated and purified by chromatography over silica gel. Mass spec. M+401(m+1, observed).

Step 2: 7β-Methyl-4-oxa-5α-Cholestan-3-one

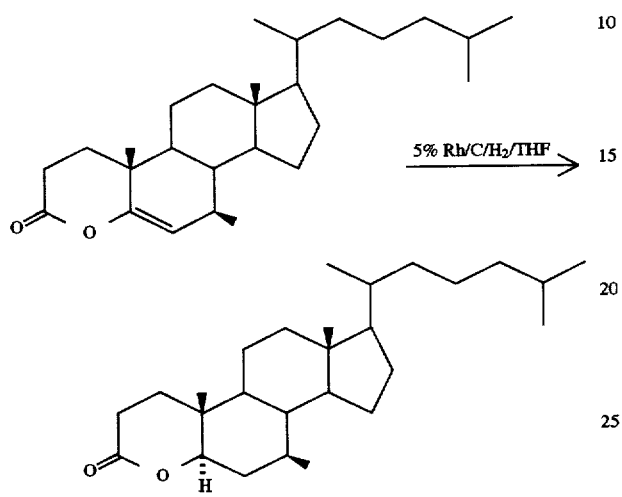

To a solution of 7β-methyl-4-oxa-Cholest-5-en-3-one (6.0 g) in THF (50 mL) was added 5% Rh/C(6.5 g). After stirring the reaction mixture under H₂ atmosphere for overnight, the mixture was flushed with N₂, filtered and concentrated. The residue was purified by chromatography over silica gel (20% ethyl acetate/hexane). Mass spec. M+403(m+1, observed).

Step 3: 7β-Methyl-4-oxa-5α-Cholest-1-en-3-one

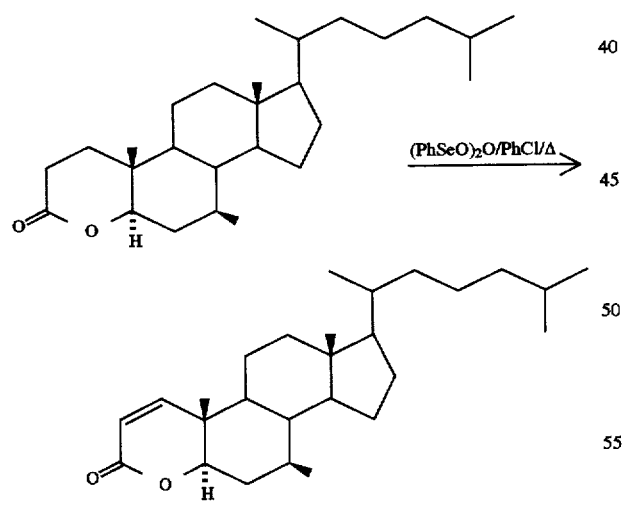

To a solution of 7β-methyl-4-oxa-5α-Cholestan-3-one (1 g, 2.49 mmol) in chlorobenzene (50 mL) was added benzeneseleninic anhydride (1.165 g, 3.24 mmol). After sting the reaction mixture at reflux temperature for overnight, the reaction mixture was diluted with ethyl acetate, washed with brine, dried and concentrated. The residue was purified by chromatography over silica gel (10% ethyl acetate/hexane). Mass spec. M+401 (m+1, observed).

EXAMPLE 8

Preparation of N-(2',5'-Bistrifluoromethylphenyl)-4-oxa-androst-1-en-3-one-17β-carboxamide Step 1  S-2'-Pyridyl-3-oxo-androst-4-ene-17β-thiocarboxylate

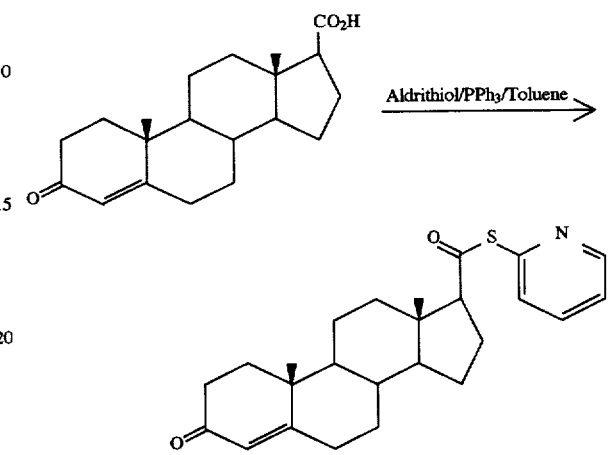

To a solution of steroid acid (10.26 g, 30 mmol) in toluene (50 mL) was added Aldrithiol (15.97 g, 72.49 mmol) and triphenylphosphine (16.88 g, 72.49 mmol). After stirring the reaction mixture for overnight at 23°, the reaction mixture was concentrated and purified by chromatography over silica gel using methylene chloride as solvent.

Step 2: N-(2',5'-Bistrifluoromethylphenyl)-3-oxo-androst-4-ene-17β-carboxamide

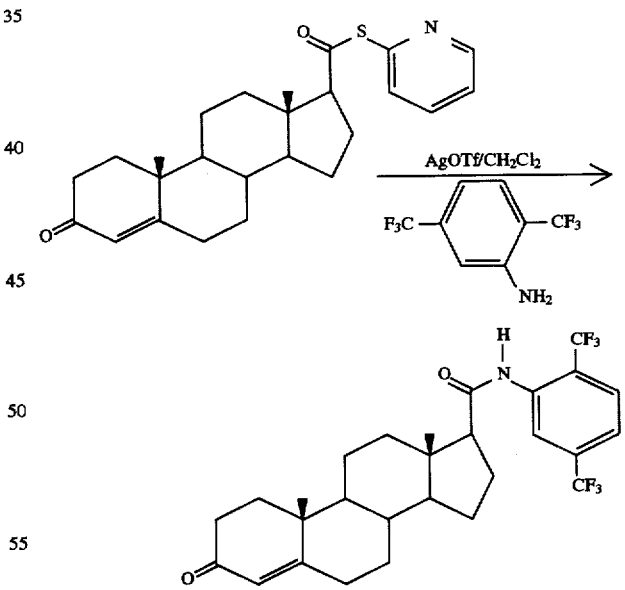

To a solution of S-2'-pyridyl-3-oxo-androst-4-ene-17β-thiocarboxylate (2.179 g, 5.19 mmol) in methylene chloride was added 2,5-bistrifluoromethylaniline (3 g, 13 mmol) and silver triflate (1.336 g, 5.2 mmol). After stirring the reaction mixture for overnight at 23°, he mixture was filtered, concentrated and purified by chromatography over silica gel using methylene chloride as solvent to give pure product.

Step 3: N-(2',5'-Bistrifluoromethylphenyl)-5-oxo-3,5-secoandrostan-3-oic-17β-carboxamide

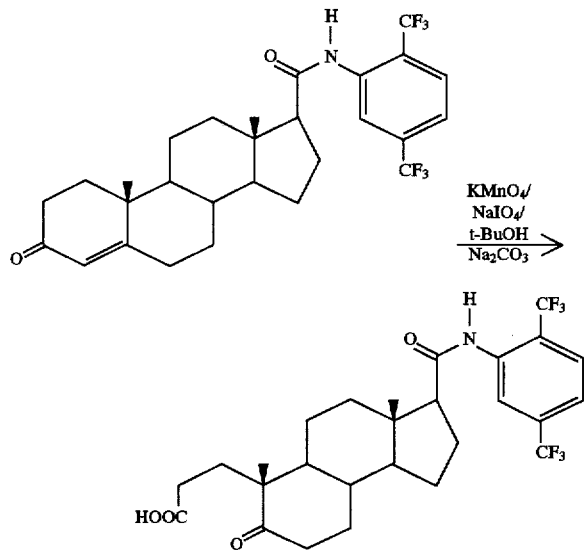

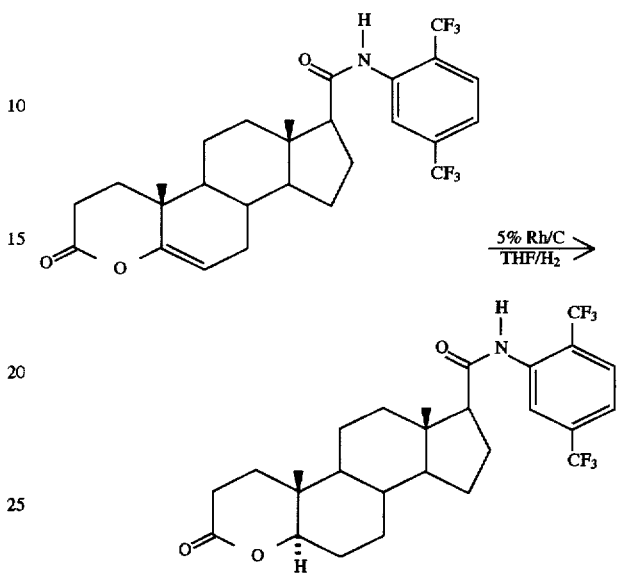

To a solution of N-(2',5'-Bistrifluoromethylphenyl)-3-oxo-androst-4-ene-17β-carboxamide(600 mg, 1.27 mmol) in t-butanol (10 mL) was added sodium carbonate (200 mg, 1.88 mmol, in 1 mL of H₂O). The reaction mixture was heated to 80° and a solution of NaIO₄ (1.81 g, 8.5 mmol) and KMnO₄ (13.2 mg, 0.08 mmol) in H₂O (10 mL) was added dropwise in ~10 minutes. After stirring the reaction mixture for 2 hrs, the mixture was cooled to room temperature and acidified to pH 2. The reaction mixture was concentrated, extracted with ethyl acetate, organic layer was dried and concentrated to give pure product Step 4: N-(2',5'-Bistrifluoromethylphenyl)-4-oxa-androst-5-en-3-one-17β-carboxamide

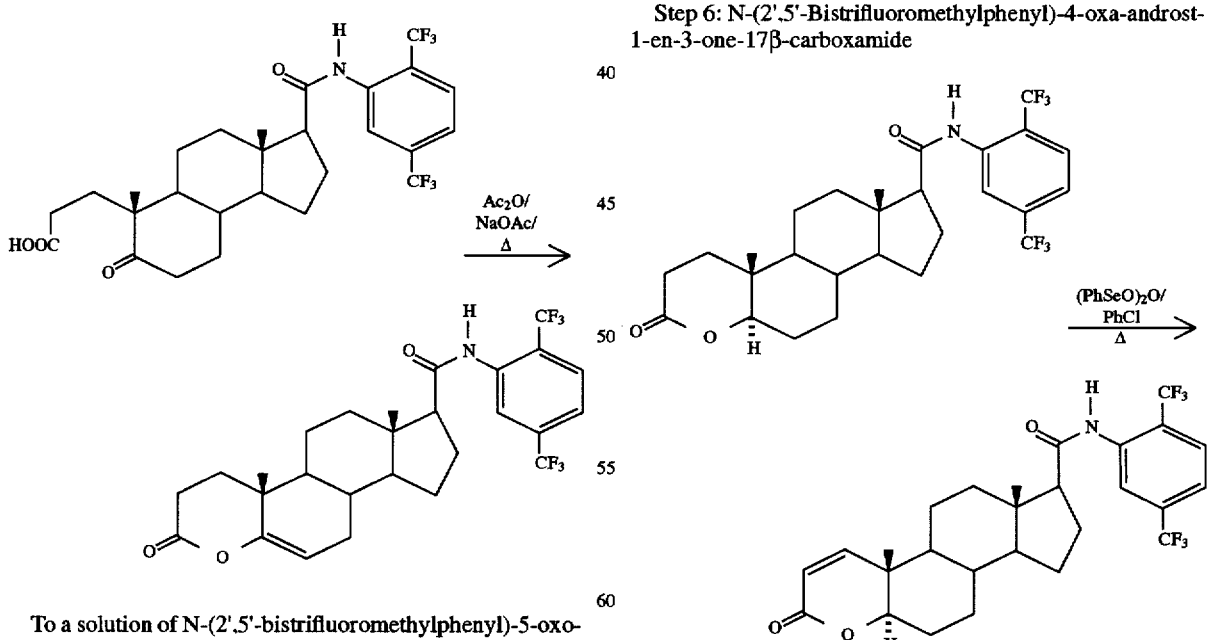

To a solution of N-(2',5'-bistrifluoromethylphenyl)-5-oxo-3,5-secoandrostan-3-oic-17β-carboxamide (600 mg, 1.19 mmol) in acetic anhydride (10 mL) was added sodium acetate ( 1.63 g, 11.9 mmol). After stirring the reaction mixture at reflux temperature for 4 hrs, the acetic anhydride was removed under vacuum and residue partitioned between ethyl acetate and water. The organic layer was washed with brine, dried, concentrated and purified by prep. tlc (5% acetone/methylene chloride). Mass spec. M⁺530 (m+1, observed).

Step 5: N-(2',5'-Bistrifluoromethylphenyl)-4-oxa-androstan-3-one-17β-carboxamide To a solution of N-(2',5'-bistrifluoromethylphenyl)-4-oxa-androst-5-en-3-one-17β-carboxamide (230 mg, 0.433 mmol) in THF (5 mL) added 5% Rh/C (200 mg). After stirring the reaction mixture for overnight under hydrogen atmosphere, the reaction mixture was flushed with nitrogen, filtered, concentrated and purified by preparative tlc (50% EtOAc/hexane) to give pare product. Mass spec. M⁺532 (m+1, observed).

Step 6: N-(2',5'-Bistrifluoromethylphenyl)-4-oxa-androst-1-en-3-one-17β-carboxamide To a solution of N-(2',5'-bistrifluoromethylphenyl)-4-oxa-androstan-3-one-17β-carboxamide. (35 mg, 0.066 mmol) in chlorobenzene (5 mL) was added benzeneseleninic anhydride (30 mg, 0.085 mmol). After stirring the reaction mixture at reflux temperature for overnight, the reaction mixture was diluted with ethyl acetate, washed with brine, dried and concentrated. The residue was purified by prep. tlc (50% EtOAc/hexane). Mass spec. M+530(m+1, observed).

EXAMPLE 9

N-t-Butyl-4-thia-5α-androst-1-en-3-one-17β-carboxamide.

Step 1: (N-Pyrid-3-yl)-5-hydroxy-3,5-secoandrostan-3-carboxamide-17β-(N-t-butyl)carboxamide.

From 500 mg of the product of step 5 of Example 6 [N-(t-butyl)-4-oxa-androstan-3-one-17β-carboxamide], the title compound is prepared by treatment with 1.25 equivalents of the dimethylaluminum complex with 3-aminopyridine by reflux in toluene for 30 min. or until the A-ring opening is shown to be complete by hplc or thin-layer chromatography. Purification is optional by column chromatography to furnish the product in good yield.

Step 2: (N-Pyrid-3-yl)-5-p-toluenesulfonyloxy-3,5-secoandrostan-3-carboxamide-17β-(N-t-butyl)carboxamide.

The product of step 1 in pyridine solution (50 mL) is cooled to 5° in ice before 1.2 equivalents of p-toluenesulfonyl chloride is added. After standing 18 hours in the refrigerator, the reaction is warmed to ambient temperature, partitioned between water and dichloromethane and washed with dilute bicarbonate solution to remove residual sulfonyl chloride. The organic layer is dried and evaporated to a residue, which is immediately taken on to the iodide displacement.

Step 3: (N-Pyrid-3-yl)-5-(epi)iodo-3,5-secoandrostan-3-carboxamide-17β-(N-t-butyl)carboxamide.

The tosyl derivative of step 2 is stirred at ambient temperature with 3 equivalents of dry tetrabutylammonium iodide in toluene for 30 min. and then heated at reflux for another 2 hrs. The reaction mixture is cooled, partitioned with dichloromethane and water, and washed to remove ammonium salts. After drying and solvent removal under reduced pressure, the residual amorphous material is chromatographed to provide the pure iodo compound.

Step 4: (N-Pyrid-3-yl)-5-acetylthio-3,5-secoandrostan-3-carboxamide-17β-(N-t-butyl)carboxamide.

The iodo compound of step 3 is stirred at ambient temperature with 10 equivalents of thioacetic acid in toluene for 30 min. and then heated at reflux for another 2 hrs. The reaction mixture is cooled, solvents and volatile reactants evaporated under reduced pressure, and the residual amorphous material chromatographed.

Step 5: N-t-Butyl-4-thia-5α-androstan-3-one-17β-carboxamide.

The thioacetyl derivative of step 4 is treated at ambient temperature with methanolic HCl (3%) until the starting material is gone by thin-layer chromatography or hplc. Product is isolated by chromatography and recrystallized.

Step 6 N-t-Butyl-4-thia-5α-androst-1-en-3-one-17β-carboxamide.

Treatment of the product of step 5 with phenylseleninic anhydride by the method of step 6 of Example 6 affords the product.

EXAMPLE 10

Oral Composition

As a specific embodiment of an oral composition of a compound of this invention, 5 mg of a compound of structural formula I of the present invention is formulated with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of the structural formula below:

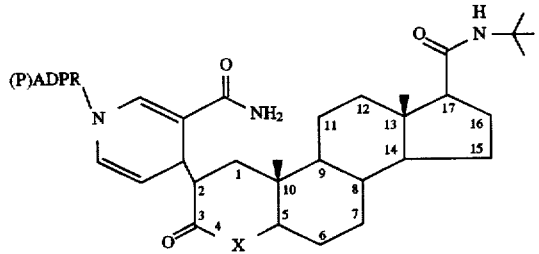

wherein: X is oxygen or sulfur and the 1,2 bond is optionally a double bond.

2. The compound of claim 1 wherein X is oxygen.

3. A method for treating benign prostatic hyperplasia in a human in need of such treatment which comprises the administration of an effective amount of the compound of claim 1.

4. A method for treating male-pattern baldness in a human in need of such treatment which comprises the administration of an effective amount of the compound of claim 1.

5. A method for the treatment of acne vulgaris in a human in need of such treatment which comprises the administration of an effective amount of the compound of claim 1.

6. A method for the treatment of seborrhea in a human in need of such treatment which comprises the administration of an effective amount of the compound of claim 1.

7. A method for the treatment of prostatic carcinoma in a human in need of such treatment which comprises the administration of an effective amount of the compound of claim 1.

8. A pharmaceutical composition comprising the covalent adduct is of structural formula

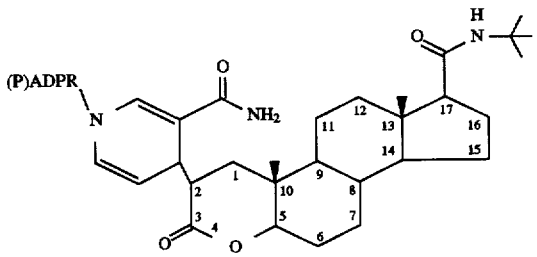

and a pharmaceutically acceptable carrier wherein the 1,2 bond is a double bond.

* * * * *